United States Patent
Iordachita et al.

(10) Patent No.: US 10,226,304 B2
(45) Date of Patent: Mar. 12, 2019

(54) SHAPE TRACKING OF A DEXTEROUS CONTINUUM MANIPULATOR

(71) Applicant: The Johns Hopkins University, Baltimore, MD (US)

(72) Inventors: Iulian Iordachita, Lutherville-Timonium, MD (US); Hao Liu, Baltimore, MD (US); Mehran Armand, Fulton, MD (US); Russell H. Taylor, Severna Park, MD (US); Amirhossein Farvardin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 358 days.

(21) Appl. No.: 14/970,177

(22) Filed: Dec. 15, 2015

(65) Prior Publication Data
US 2016/0166341 A1   Jun. 16, 2016

Related U.S. Application Data

(60) Provisional application No. 62/092,070, filed on Dec. 15, 2014, provisional application No. 62/169,307, filed on Jun. 1, 2015.

(51) Int. Cl.
*A61B 34/30* (2016.01)
*G01B 11/24* (2006.01)
(Continued)

(52) U.S. Cl.
CPC .............. *A61B 34/30* (2016.02); *A61B 34/35* (2016.02); *A61B 34/71* (2016.02); *G01B 11/165* (2013.01);
(Continued)

(58) Field of Classification Search
CPC .......... A61B 34/30; A61B 34/35; A61B 34/71; G01B 11/165; G01B 11/24
See application file for complete search history.

(56) References Cited

U.S. PATENT DOCUMENTS 5,194,847 A * 3/1993 Taylor ..................... G01H 9/004
                                                           340/541
5,633,494 A * 5/1997 Danisch ............ G02B 6/02057
                                                           250/227.14
(Continued)

OTHER PUBLICATIONS

Araújo et al., "Temperature and strain insensitive bending measurements with D-type fibre Bragg gratings," Measurement Science and Technology, vol. 12, pp. 829-833, 2001.
(Continued)

*Primary Examiner* — Patrick H Mackey
(74) *Attorney, Agent, or Firm* — Venable LLP; Henry J. Daley; Laura G. Remus

(57) ABSTRACT

A shape sensor system includes a deflection sensor comprising an optical fiber having at least one fiber Bragg grating (FBG) written therein and a substrate, the fiber being attached to the substrate with a selected bias distance from a neutral plane of the deflection sensor. The system further includes an optical source coupled to the fiber to provide input light to be at least partially reflected by the FBG, and an optical detection and processing system arranged to receive at least a portion of the output light and to determine a wavelength shift resulting from a change of an amount of deflection of the deflection sensor. The optical detection and processing system determines a relative amount of deflection of the deflection sensor at the FBG based on the wavelength shift. The selected bias distance is selected based on an expected range of deflection angles to be detected.

5 Claims, 22 Drawing Sheets

(51) Int. Cl.
*G01B 11/16* (2006.01)
*A61B 34/00* (2016.01)
*A61B 34/35* (2016.01)
*A61B 34/20* (2016.01)

(52) U.S. Cl.
CPC ...... *G01B 11/24* (2013.01); *A61B 2034/2061* (2016.02); *A61B 2034/301* (2016.02); *A61B 2034/306* (2016.02)

(56) References Cited

U.S. PATENT DOCUMENTS

| | | | | |
|---|---|---|---|---|
| 7,073,387 B2* | 7/2006 | Zdeblick | ............ | A61B 5/0215 73/715 |
| 8,121,687 B2* | 2/2012 | Jensen | ............ | A61B 5/1107 607/17 |
| 8,257,991 B1* | 9/2012 | Park | ............ | G01D 3/0365 250/227.11 |
| 9,259,278 B2* | 2/2016 | Jensen | ............ | A61B 6/4405 |
| 2002/0092976 A1* | 7/2002 | Sugai | ............ | G01L 1/246 250/227.14 |
| 2004/0197050 A1* | 10/2004 | Lovseth | ............ | G01B 11/16 385/37 |
| 2005/0232532 A1* | 10/2005 | Wang | ............ | A61B 5/6892 385/13 |
| 2008/0033442 A1* | 2/2008 | Amiot | ............ | A61B 5/1077 606/80 |
| 2008/0285909 A1* | 11/2008 | Younge | ............ | A61B 5/1076 385/13 |
| 2011/0319714 A1* | 12/2011 | Roelle | ............ | A61B 1/00006 600/118 |
| 2015/0224275 A1* | 8/2015 | Pastoor | ............ | A61M 16/0611 128/205.25 |

OTHER PUBLICATIONS

Camarillo et al., "Mechanics Modeling of Tendon-Driven Continuum Manipulators," IEEE Transactions On Robotics, vol. 24, No. 6, pp. 1262-1273, 2008.
Chen et al., "Highly Sensitive Bend Sensor Based on Bragg Grating in Eccentric Core Polymer Fiber," IEEE Photonics Technology Letters, vol. 22, No. 11, pp. 850-852, 2010.
Cianchetti et al., "Sensorization of continuum soft robots for reconstructing their spatial configuration," The Fourth IEEE RAS/EMBS International Conference on Biomedical Robotics and Biomechatronics, Roma, Italy, Jun. 24-27, 2012, pp. 634-639.
Engh et al., "The Quality of Osteolysis Grafting with Cementless Acetabular Component Retention," Clinical Orthopaedics and Related Research, No. 465, pp. 150-154, 2007.
Esposito et al., "Fiber Bragg Grating sensors to measure the coefficient of thermal expansion of polymers at cryogenic temperatures," Sensors and Actuators A: Physical, 2013, 189, pp. 195-203.
Franz et al., "Electromagnetic Tracking in Medicine—a Review of Technology, Validation and Applications," IEEE Transactions on Medical Imaging, vol. 33, No. 8, Aug. 2014.
He et al., "A Submillimetric 3-DOF Force Sensing Instrument With Integrated Fiber Bragg Grating for Retinal Microsurgery," IEEE Transactions on Biomedical Engineering, vol. 61, No. 2, pp. 522-534, Feb. 2014.
Ikuta et al., "Development of Remote Microsurgery Robot and New Surgical Procedure for Deep and Narrow Space," Proceedings of the 2003 IEEE International Conference on Robotics and Automation, Taipei, Taiwan, Sep. 14-19, 2003, pp. 1103-1108.
Kutzer et al., "Design of a New Cable-Driven Manipulator with a Large Open Lumen: Preliminary Applications in the Minimally-Invasive Removal of Osteolysis," 2011 IEEE International Conference on Robotics and Automation, May 9-13, pp. 2913-2920.
Lee et al., "Enhanced temperature sensitivity of fiber Bragg grating temperature sensor using thermal expansion of copper tube," Microwave and Optical Technology Letters, vo. 53, No. 7, Jul. 2011, pp. 1669-1671.
Liu et al., "Large Deflection Shape Sensing of a Continuum Manipulator for Minimally-Invasive Surgery," 2015 IEEE International Conference on Robotics and Automation (ICRA), Washington State Convention Center, Seattle, Washington, May 26-30, 2015, pp. 201-206.
MacPherson et al., "Tunnel monitoring using multicore fibre displacement sensor," Measurement Science and Technology, vol. 17, pp. 1180-1185, 2006.
Moon et al., "Fiber-Bragg-grating-based ultrathin shape sensors displaying single-channel sweeping for minimally invasive surgery," Optics and Lasers in Engineering, vol. 59, pp. 50-55, Aug. 2014.
Moore et al., "Shape sensing using multi-core fiber optic cable and parametric curve solutions," Optics Express, vol. 20, No. 3, pp. 2967-2973.
Murphy et al., "Constrained Workspace Generation for Snake-like Manipulators with Applications to Minimally Invasive Surgery," 2013 IEEE International Conference on in Robotics and Automation (ICRA), Karisruhe, Germany, May 6-10, 2013, pp. 5341-5347.
Otake et al., "Model-based Cone-Beam CT Reconstruction for Image-Guided Minimally Invasive Treatment of Hip Osteolysis," SPIE, vol. 8671, pp. 86710Y-86710Y-7, 2013.
Otake et al., "Piecewise-rigid 2D-3D Registration for Pose Estimation of Snake-like Manipulator using an Intraoperative X-ray Projection," SPIE, vol. 9036, pp. 90360Q-90360Q.
Park et al., "Real-time Estimation of 3-D Needle Shape and Deflection for MRI-Guided Interventions," IEEE/ASME Transactions on Mechatronics, vol. 15, No. 6, Dec. 2010, pp. 906-915,.
Reynaerts et al., "Shape memory micro-actuation for a gastrointestinal intervention system," Sensors and Actuators, vol. 77, pp. 157-166, 1999.
Roesthuis et al., "Three-Dimensional Needle Shape Reconstruction Using an Array of Fiber Bragg Grating Sensors," IEEE/ASME Transactions on Mechatronics, vol. 19, No. 4, Aug. 2014, pp. 1115-1126.
Ryu et al., "FBG-based Shape Sensing Tubes for Continuum Robots," IEEE International Conference on Robotics & Automation (ICRA), Hong Kong Convention and Exhibition Center, May 31-Jun. 7, 2014, pp. 3531-3537.
Sears et al., "Inverse Kinematics of Concentric Tube Steerable Needles," 2007 IEEE International Conference on Robotics and Automation, Roma, Italy, Apr. 10-14, 2007, pp. 1887-1892.
Segreti et al., "Cable Length Estimation for a Compliant Surgical Manipulator,", 2012 IEEE International Conference on Robotics and Automation (ICRA), May 14-18, 2012, pp. 701-708.
Shapiro et al., "Shape Tracking of Planar Hyper-Flexible Beams via Embedded PVDF Deflection Sensors," IEEE/ASME Transactions on Mechatronics, vol. 19, No. 4, Aug. 2014, pp. 1260-1267.
Simaan et al., "High dexterity snake-like robotic slaves for minimally invasive telesurgery of the upper airway," in Medical Image Computing and Computer-Assisted Intervention-MICCAI 2004, Springer, 2004, pp. 17-24.
Webster et al., "Mechanics of Precurved-Tube Continuum Robots," IEEE Transactions on Robotics, vol. 25, No. 1, Feb. 2009, pp. 67-78.
Yi et al., "An innovative 3D colonoscope shape sensing sensor based on FBG sensor array," in Information Acquisition, 2007. ICIA'07. International Conference on, pp. 227-232, 2007.
Murphy et al., "Design and kinematic characterization of a surgical manipulator with a focus on treating osteolysis," Robotica, pp. 1-16, 2013.

* cited by examiner

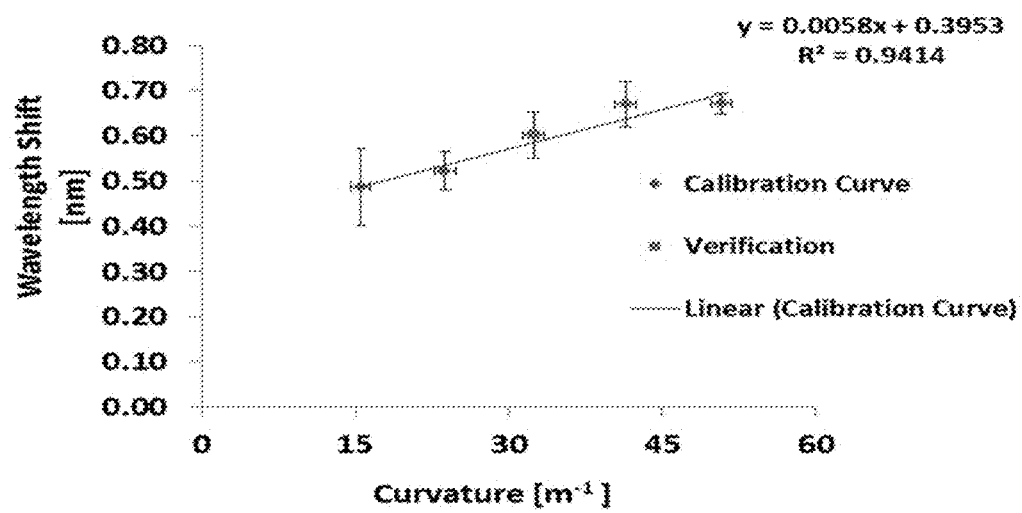
FIG. 12
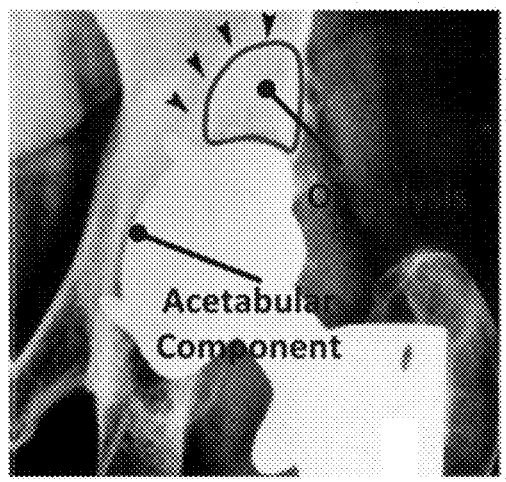 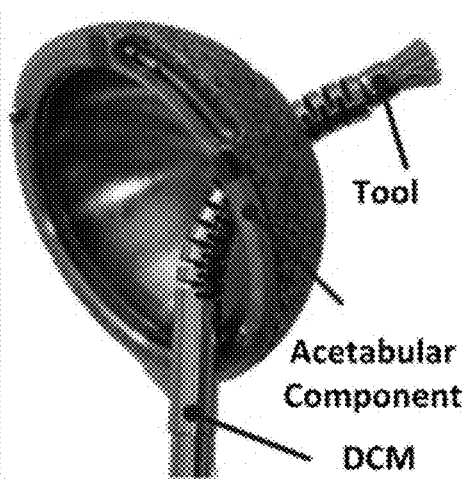
FIG. 13A    FIG. 13B

SHAPE TRACKING OF A DEXTEROUS CONTINUUM MANIPULATOR

This application claims priority to U.S. Provisional Application No. 62/092,070 filed Dec. 15, 2014, and to U.S. Provisional Application No. 62/169,307 filed Jun. 1, 2015, the entire content of which is hereby incorporated by reference.

This invention was made with U.S. Government support under grant numbers EB 016703 and CA 111288 awarded by the Department of Health and Human Services, The National Institutes of Health (NIH). The U.S. Government has certain rights in the invention.

BACKGROUND

1. Technical Field

The field of the currently claimed embodiments of this invention relates to dexterous continuum manipulators, and more particularly systems and methods for shape tracking of a dexterous continuum manipulator.

2. Discussion of Related Art

Flexible instruments and dexterous continuum manipulators (DCMs) are commonly used in minimally-invasive surgery (MIS) for their high steerability and capability to increase the operation space within limited anatomical regions. Several groups have proposed a variety of surgical dexterous manipulators. Examples include active cannulae composed from a series of nested and curved tubes, shape memory actuation units, and cable-driven manipulators.

SUMMARY

According to some embodiments of the present invention, a shape sensor system includes a deflection sensor comprising an optical fiber having at least one fiber Bragg grating (FBG) written therein and a substrate, the optical fiber being attached to the substrate with a selected bias distance from a neutral plane of the deflection sensor. The shape sensor system further includes an optical source optically coupled to the optical fiber to provide input light to be at least partially reflected by the FBG to provide output light, and an optical detection and processing system arranged to receive at least a portion of the output light and to determine a wavelength shift of at least a portion of the output light resulting from a change of an amount of deflection of the deflection sensor. The optical detection and processing system is further configured to determine a relative amount of deflection of the deflection sensor at the FBG based on the wavelength shift. The selected bias distance is selected based on an expected range of deflection angles to be detected.

According to some embodiments of the present invention, a flexible device includes a flexible elongated portion of the flexible device having a first end and a second end. The flexible device further includes a shape sensor system that includes a deflection sensor comprising an optical fiber having at least one FBG written therein and a substrate, the optical fiber being attached to the substrate with a selected bias distance from a neutral plane of the deflection sensor. The shape sensor system further includes an optical source optically coupled to the optical fiber to provide input light to be at least partially reflected by the FBG to provide output light, and an optical detection and processing system arranged to receive at least a portion of the output light and to determine a wavelength shift of at least a portion of the output light resulting from a change of an amount of deflection of the deflection sensor. The optical detection and processing system is further configured to determine a relative amount of deflection of the deflection sensor at the FBG based on the wavelength shift. The selected bias distance is selected based on an expected range of deflection angles to be detected, and the deflection sensor of the shape sensor system is slidably connected to the flexible elongated portion of the flexible device extending from the first end to the second end.

According to some embodiments of the present invention, a deflection sensor includes a substrate and an optical fiber attached to the substrate to have a selected bias distance from a neutral plane of the deflection sensor. The optical fiber has at least one FBG written therein.

According to some embodiments of the present invention, a dexterous continuum manipulator (DCM) system includes a DCM having a distal end and a proximal end, a signal processor configured to be in communication with the DCM, and a display device configured to be in communication with the signal processor. The DCM includes a first shape sensor attached at the distal end of the DCM and extending through a first lumen along a first side of the DCM to be slidable within the first lumen and at the proximal end of the DCM. The DCM further includes a second shape sensor attached at the distal end of the DCM and extending through a second lumen along a second side of the DCM to be slidable within the second lumen and at the proximal end of the DCM. The signal processor is configured to calculate a shape curve of each of the first and second shape sensors starting at the distal end of the DCM, offset each of the shape curves to a point on a centerline of the DCM, and extrapolate at least one of the shape curves to obtain shape curves of equal length. The signal processor is further configured to calculate a centerline between the shape curves of equal length, extrapolate the centerline to a predetermine length of the DCM, and determine a tangential direction of a proximal point of the centerline and assign an orthogonal coordinate system at the proximal point. The signal processor is further configured to form a transformation matrix between the distal point and the proximal point of the centerline, transform the centerline in a space using the transformation matrix, and offset the centerline in each of at least two opposing directions substantially orthogonal to the centerline by a predetermined amount to establish one of a two dimensional or three dimensional calculated outline of the DCM.

According to some embodiments of the present invention, a method is provided for determining a shape of a DCM based on a plurality of shape sensors, the DCM having a distal end and a proximal end and including a first shape sensor attached at the distal end of the DCM and extending through a first lumen along a first side of the DCM to be slidable within the first lumen and at the proximal end of the DCM, and a second shape sensor attached at the distal end of the DCM and extending through a second lumen along a second side of the DCM to be slidable within the second lumen and at the proximal end of the DCM. The method includes calculating a shape curve of each of the first and second shape sensors starting at the distal end of the DCM and offsetting each of the shape curves to a point on a centerline of the DCM, extrapolating at least one of the shape curves to obtain shape curves of equal length, and calculating a centerline between the shape curves of equal length. The method further includes extrapolating the centerline to a predetermined length of the DCM, determining a tangential direction of a proximal point of the centerline and assigning an orthogonal coordinate system at the proximal point, and forming a transformation matrix between the distal point and the proximal point of the centerline. The method further includes transforming the centerline in a space using the transformation matrix, and offsetting the centerline in each of at least two opposing directions substantially orthogonal to the centerline by a predetermined amount to establish one of a two dimensional or three dimensional calculated outline of the DCM.

BRIEF DESCRIPTION OF THE DRAWINGS

Further objectives and advantages will become apparent from a consideration of the description, drawings, and examples.

FIG. 12 shows a mean wavelength shift for different curvatures, calibration (diamonds) and verification (squares);

FIG. 13A shows a hip with osteolysis;

FIG. 13B shows a DCM with a tool entering through a screw hole on the acetabular cup;

DETAILED DESCRIPTION

Figure 1A:
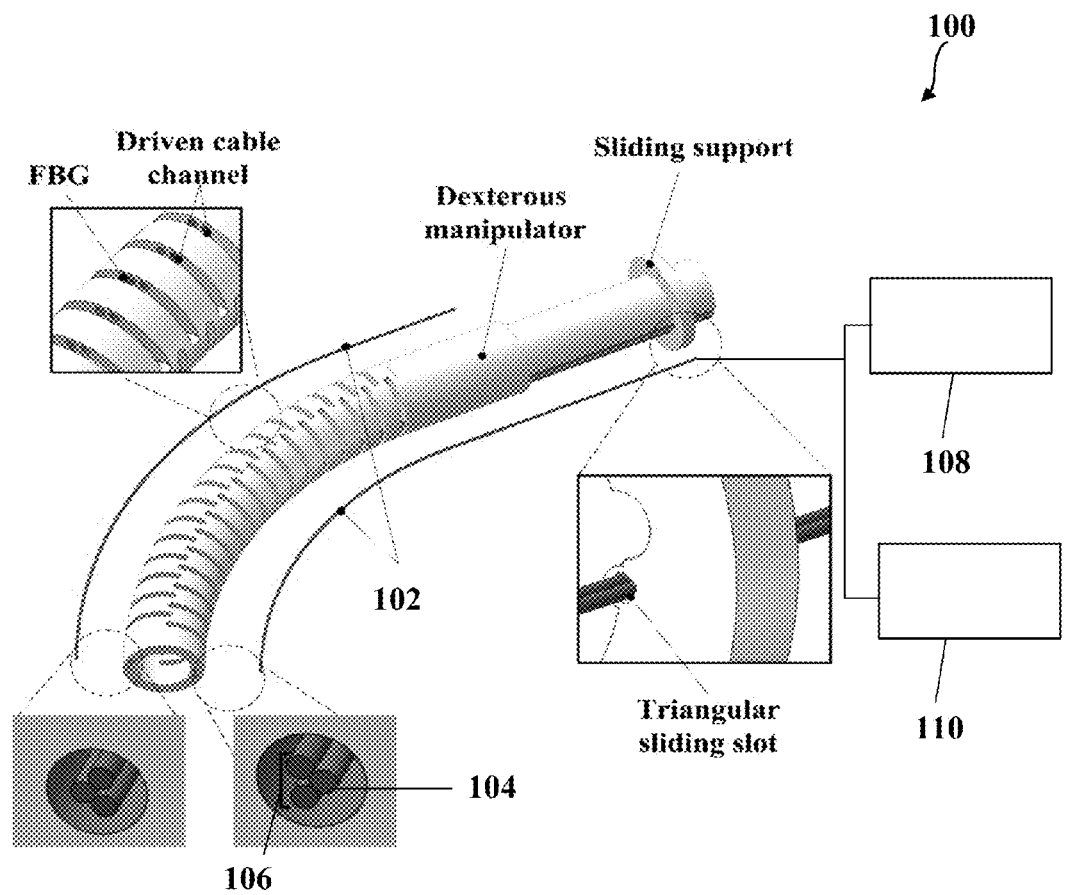
FIG. 1A is a schematic illustration of a shape sensor system according to some embodiments of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention are directed to systems and methods for determining a shape of a dexterous continuum manipulator.

The terms "light" and "optical" are intended to have a broad definition to include both visible and non-visible regions of the electromagnetic spectrum. For example, near infrared, infrared, and ultraviolet regions of the electromagnetic spectrum, in addition to visible light, are intended to be included within the definition of these terms.

The term "neutral plane" means the surface within the beam where the material of the beam is not under stress, either compression or tension.

The term "large deflection" for a DCM means shape configurations in which the curvature of the DCM is larger than the curvature associated with the maximum strain or stress the optical fiber could withstand if it were bonded directly to the DCM. The curvature of the DCM is generally considered to be the curvature of the osculating circle at a given point on the DCM. The curvature of a circle is defined as the inverse of its radius, and thus circles of smaller radius have greater curvature. Herein, greater curvature, or deflection, is meant to indicate a curve whose osculating circle has a smaller radius, i.e., a "tighter" curve.

Some embodiments of the current invention are directed to dexterous continuum manipulator (DCM) shape sensing and, more particularly, to large deflection shape sensing for DCM. A large deflection refers to a curvature the sensor could detect before it breaks due to certain large strain (stress), ranging from that when the sensor is bonded to the DCM to that of the sensor itself. DCMs have found a variety of applications in robotic surgery in general and, specifically, in minimally-invasive surgery (MIS). These DCMs typically assist surgeons in diagnosis and/or operating in constrained environments. For many surgical applications, the DCMs may need to operate with curvatures much larger than the current shape sensing methods can detect. An embodiment of this invention concerns shape sensing techniques utilizing Fiber Bragg grating (FBG) arrays which can detect the curvature of DCM with large deflection (large curvature and large angle of curvature). For this purpose, we used FBG sensors along with nitinol wires as the supporting substrates to form a triangular cross section according to an embodiment of the current invention. More generally, the shape sensing techniques can enable real-time tracking and control of DCMs used in MIS.

Some aspects of the current invention are directed to the following:

1. The sensing principle of the large deflection shape sensor is strain-gauge based. In our implementation, fiber optical sensors, i.e. fiber Bragg gratings, are used. However, other strain sensing technologies can also be adopted to realize the large deflection shape sensing (e.g., strain gauges, Fabry-Perot interferometers, and any other strain sensor that could be made compact enough to fit into the DCM body). These sensors can be assembled in series and have the similar configuration and same function as the shape sensor shown in the examples. The large deflection shape sensor is composed of fiber optical sensors (single or multi fiber FBG) and substrate wire/s. They are bonded together to make the FBG core biased from the neutral plane of the assembly. The sensitivity of the sensor can be changed by adjusting relative position of substrate wires. The sensor also has a non-uniform circumferential elastic bending modulus which can facilitate anti-twisting function. It can precisely detect its curvature in large deflection range, and display its shape in real-time. The sensor can also be made MRI-compatible.

2. The 2D or 3D shape sensing scheme for dexterous manipulators insert single or multi shape sensors through the dexterous manipulators' lumens (or channels). The tensioned shape sensors are fixed at the distal end to the manipulator's body and are allowed to freely move along with the bending of the dexterous manipulator, which is different from existing solutions where the whole sensors body is fixed to the dexterous manipulator. It can precisely detect the shape of the dexterous manipulators and flexible instruments in large deflection, in real-time.

The control protocol and algorithms described herein may be implemented by a processor. The processor may be referred to as signal processor, or may include an optical detection apparatus, and may be referred to as an optical detection and processing system. The processor can be a dedicated "hard-wired" device, or it can be a programmable device. For example, it can be, but is not limited to, a personal computer, a work station, or any other suitable electronic device for the particular application. In some embodiments, it can be integrated into a unit or it can be attachable, remote, and/or distributed.

A shape sensor system according to some embodiments of the current invention is illustrated schematically in FIG. 1A. The broad concepts of the current invention are not limited to only this embodiment. According to some embodiments, the shape sensor system 100 includes a deflection sensor 102 comprising an optical fiber 104 having at least one fiber Bragg grating written therein and a substrate 106, the optical fiber 104 being attached to the substrate 106 with a selected bias distance from a neutral plane of the deflection sensor 102. The shape sensor system 100 further includes an optical source 108 optically coupled to the optical fiber 104 to provide input light to be at least partially reflected by the FBG to provide output light. The optical sensing system 100 also includes an optical detection and processing system 110 arranged to receive at least a portion of the output light and to determine a wavelength shift of at least a portion of the output light resulting from a change of an amount of deflection of the deflection sensor 102, the optical detection and processing system 110 being further configured to determine a relative amount of deflection of the deflection sensor 102 at the FBG based on the wavelength shift. According to some embodiments, the selected bias distance is selected based on an expected range of deflection angles to be detected. According to some embodiments, the substrate 106 is a pair of wires attached to the optical fiber in a triangular configuration as viewed from a cross section thereof. The distance between the pair of wires in the triangular configuration can be selected to obtain the selected bias distance.

Figure 1B:
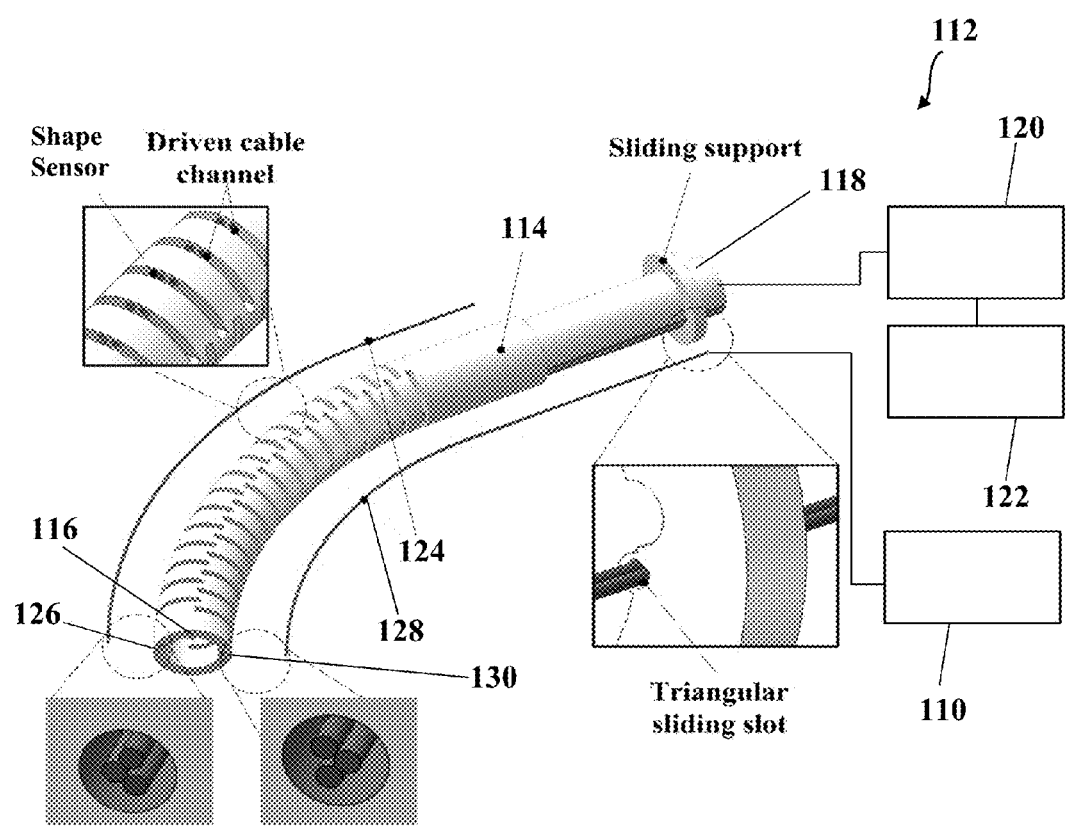
FIG. 1B is a schematic illustration of a dexterous continuum manipulator (DCM) system according to some embodiments of the invention.

A DCM system 112 according to some embodiments of the current invention is illustrated schematically in FIG. 1B. The DCM system 112 includes a DCM 114 having a distal end 116 and a proximal end 118, a signal processor 120 configured to be in communication with the DCM 114, and a display device 122 configured to be in communication with the signal processor 120. The DCM 114 includes a first shape sensor 124 attached at the distal end 116 of the DCM 114 and extending through a first lumen 126 along a first side of the DCM to be slidable within the first lumen 126 and at the proximal end 118 of the DCM 114. The DCM 114 also includes a second shape sensor 128 attached at the distal end 116 of the DCM 114 and extending through a second lumen 130 along a second side of the DCM 114 to be slidable within the second lumen 130 and at the proximal end 118 of the DCM 114

The signal processor 120 is configured to calculate a shape curve of each of the first and second shape sensors 124, 128 starting at the distal end 116 of the DCM 114. The signal processor 120 is further configured to offset each of the shape curves to a point on a centerline of the DCM 114. The signal processor 120 is further configured to extrapolate at least one of the shape curves to obtain shape curves of equal length. The signal processor 120 is further configured to calculate a centerline between the shape curves of equal length, and extrapolate the centerline to a predetermine length of the DCM 114. The signal processor 120 is further configured to determine a tangential direction of a proximal point of the centerline and assign an orthogonal coordinate system at the proximal point, and form a transformation matrix between the distal point and the proximal point of the centerline. The signal processor 120 is further configured to transform the centerline in a space using the transformation matrix, and offset the centerline in each of at least two opposing directions substantially orthogonal to the centerline by a predetermined amount to establish one of a two dimensional or three dimensional calculated outline of the DCM 114.

The following examples describe some embodiments in more detail. The broad concepts of the current invention are not intended to be limited to the particular examples. Further, concepts from each example are not limited to that example, but may be combined with other embodiments of the system.

EXAMPLES

Example 1

Large Deflection Shape Sensing of a Continuum Manipulator for Minimally-Invasive Surgery Flexible instruments and dexterous continuum manipulators (DCMs) are commonly used in minimally-invasive surgery (MIS) for their high steerability and capability to increase the operation space within limited anatomical regions. Several groups have proposed a variety of surgical dexterous manipulators. Examples include active cannulae composed from a series of nested and curved tubes [1, 2], shape memory actuation units [3], and cable-driven manipulators [4-6].

Figure 2:
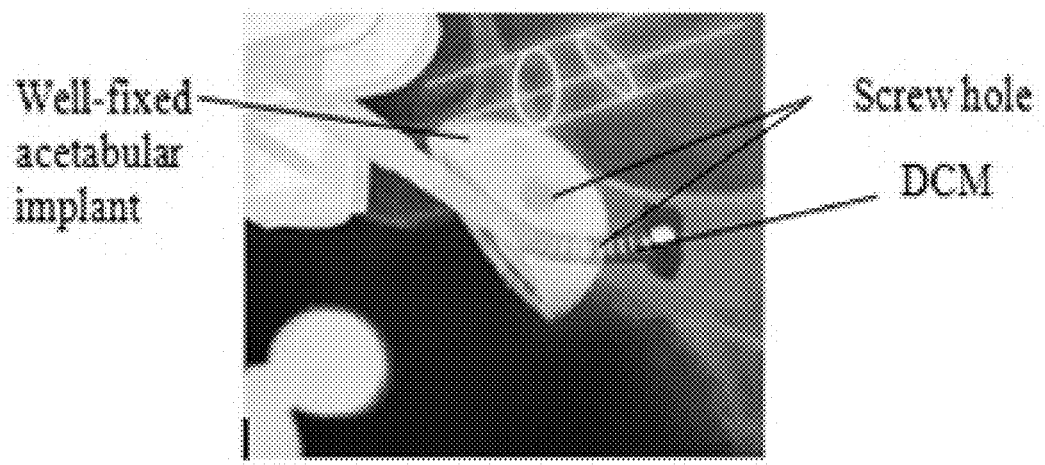
FIG. 2 illustrates minimally-invasive surgery (MIS) treatment of osteolysis.

We have previously developed a cable-driven DCM for the MIS treatment of osteolysis occurring after total hip arthroplasties [7]. The goal of this surgery is to remove and replace the bone defect caused by polyethylene liner of an acetabular implant. Without removing the well-fixed acetabular implant, the MIS approach uses the holes in the implant to access the osteolytic lesion (FIG. 2). We have previously reported the design and development of a cable driven DCM with a 6 mm outer diameter which was built from two nested nitinol tubes. The major features of this DCM for orthopedics applications include relatively large inner to outer diameter ratio (4 mm/6 mm) and relative structural strength in the plane orthogonal to its bending plane. These features enable inserting custom-designed tools (e.g. cutter, gripper, curette, flexible endoscope) through the lumen of the DCM for the proposed procedure as well as other similar MIS applications.

Previous efforts for intraoperative control of the DCM involved developing models for estimating the shape from cable-length measurements [8, 9], as well as the intermittent use of x-ray for updating the model estimation [10]. This approach would, however, require a trade-off between accurate real-time control and the amount of x-ray exposure to the patient. Real-time shape sensing would reduce the reliance on using intermittent x-rays for estimating the shape of the DCM.

Approaches for shape sensing may include the use of electromagnetic sensors. In the presence of metal implants and tools, however, electromagnetic interference will limit the accuracy of the sensors [11]. Also, these sensors usually have a rigid body and cannot adapt to the continuous bending of the instruments or robots, especially for a small continuum robot [9]. In addition, the tracking frequency is limited to less than 50 Hz.

Fiber-optic sensors offer a number of advantages over conventional sensors, including the absence of electromagnetic interference, lightweight structures, stability, repeatability, high sensitivity, fast response, integrated structure, and a potentially low cost. Owing to their intrinsic characteristics, FBGs are particularly well suited for measuring strain with a high bending sensitivity. By analyzing the reflected wavelength from each fiber, the curvature and bending direction can be obtained.

Two different approaches are commonly used for curvature detection with FBG sensors: 1) integrating the sensor with a substrate to form an assembly (e.g. [12, 13]), and 2) creating a bundle of sensors and optical fibers (e.g. [14, 15]).

For both approaches, maximizing detection range has rarely been considered in the literature. In Table 1, we have summarized some approaches and their detection ranges. For our proposed DCM, the largest bending radius can reach to approximately 6 mm, where the curvature is about 166.7 $m^{-1}$. As shown in Table 1, this value is much larger than what current methods of shape sensing can measure. To detect relatively large curvatures, it is not possible to directly connect the FBG sensor to the DCM (i.e., approach 1), because the bending strains of the DCM are much higher than what optical fibers can handle. Therefore, a special supporting structure may be required to reduce the bending strain of the optical fiber for large curvature bending.

By using Multi-core fibers, eccentric-core fibers, and D-shape fibers (approach 2), we can reduce the bending strain to a fairly small value. This, however, may cause light interference for the multi-core fiber or reduce the stiffness of the D-shape sensor. It is also challenging to prevent these sensors from twisting.

TABLE 1

Existing shape sensing methods with FBG sensors

| Author | Type | Max Curvature (mm$^{-1}$) |
| --- | --- | --- |
| X. Yi et al. [16] | 4 FBG sensors with nitinol wire | 8 |
| Y. L. Park et al. [12] | 3 FBG sensors with grooved nitinol wire | 2 |
| R. J. Roesthuis et al.[17] | 3 FBG sensors with grooved nitinol wire | 10 |
| W N MacPherson et al. [13] | Multi-core FBG sensor | 22.7 |
| X. Chen et al. [14] | Eccentric FBG sensor | 3.5 |
| F M Araujo et al. [15] | D-shape FBG sensor | 10 |

Generally, the shape of the sensor is obtained from interpolation of discrete FBG strain data along the arc length. Because of this, the configuration of the FBG sensor should be properly designed to meet requirements of large curvature detection for our DCM. The basic principle of curvature detection is as follows:

$$\Delta\lambda = \kappa_\varepsilon \varepsilon + \kappa_T \Delta T \quad (1)$$

$$\varepsilon = \Delta \cdot \rho \quad (2)$$

where $\varepsilon$ is the strain for FBG sensor, $\Delta$ is the bias distance of the optical fiber from the neutral plane of the sensor (FIG. 3), $\rho$ is the curvature of the body being tested, $\Delta\lambda$ is the wavelength shift, $\kappa_\varepsilon$ is the strain coefficient, and $\kappa_T$ is the temperature coefficient.

Figure 3:
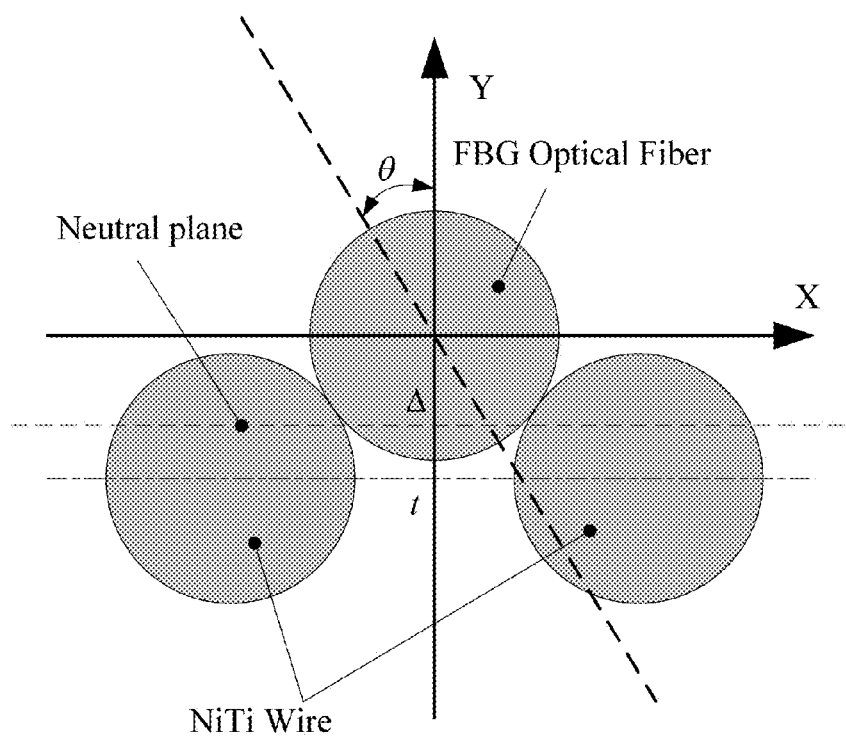
FIG. 3 shows a sensor configuration for larger curvature detection.

If temperature is well compensated, the wavelength shift of FBG optical fiber is proportional to the strain as well as the curvature. Therefore, the maximum curvature is largely dependent on $\Delta$ which should be kept as small as possible. Accordingly, the bias distance is selected based on an expected range of deflection angles to be detected. In contrast to making the core biased or cladding asymmetrical within the optical fibers, our sensor is designed with one FBG optical fiber and two nitinol wires that are bonded together, as shown in FIG. 3.

The dimensional requirements are as follows:

(a) The FBG allowable strain requires the FBG fibers to be located near the neutral plane of the SSA. FBG fibers should work within certain strain range. Previously it was shown that optical fibers can handle strain values that are less than 0.5% [15]. Herein, we have used FBG fibers that can measure up to 1% strain without breaking;

(b) In order to distinguish wavelengths for all FBG sensing points, the wavelength ranges must ideally have no overlap. The wave length range for the used interrogator was 40 nm (Micron Optics, USA). However, some overlap will enable employing more FBG sensing points within the wavelength range and, therefore, provide higher shape sensing precision.

In our design, the SSAs are allowed to freely move along with the bending plane of the DCM. The neutral plane of the DCM is located at the centerline of the DCM, and the distance from FBG fiber centerline to the neutral plane is about 2.5 mm. This distance will result in an unbearable strain for the FBG fibers. The shape sensor, therefore, is bonded to its own substrate, allowing it to freely move along the DCM during bending. This will result in greatly reducing the bias distance between the FBG fiber centerline and its neutral plane.

The nitinol wires prevent local stress concentration. Different materials can be used for this application, but considering the allowable strain under large deformation, nitinol is the most suitable choice for this application. As a result of its superelasticity property, nitinol works in its elastic region (with constant modulus) within the allowable strain range of the optical fiber.

Figures 4A, 4B:
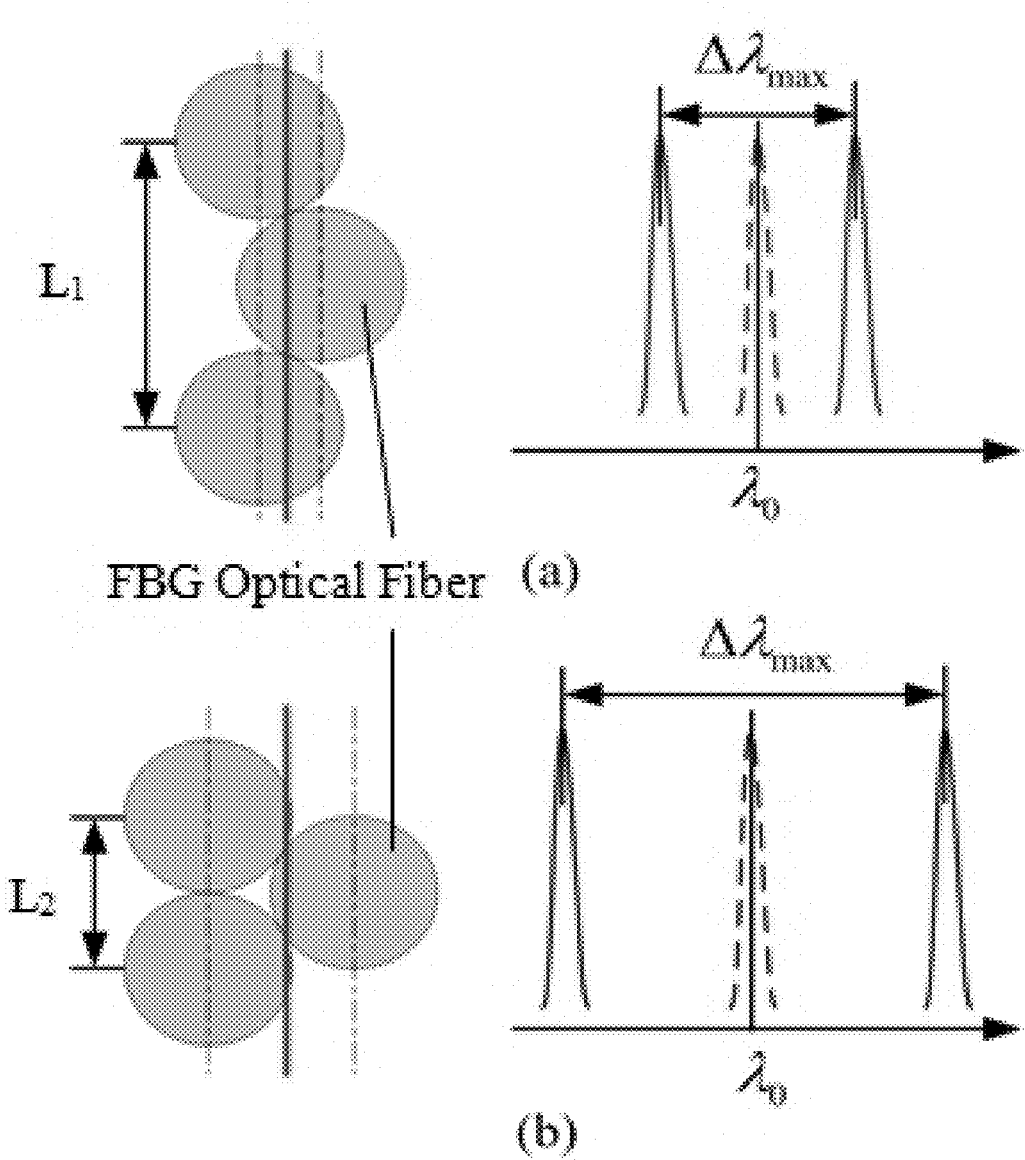
FIG. 4A shows a strategy to reduce the range of wavelength shift by increasing the center distance between NiTi wires (L1>L2) as compared to that of FIG. 4B.
FIG. 4B shows a configuration in which the center distance between the NiTi wires is minimized.

The FBG center line to the SSA neutral plane distance can be adjusted to a small value by changing the relative distance of two nitinol wires, as shown in FIG. 4. The triangular cross section of the SSA (shown in FIG. 3) has a non-uniform elastic bending modulus which keeps the SSA from twisting.

Figure 5:
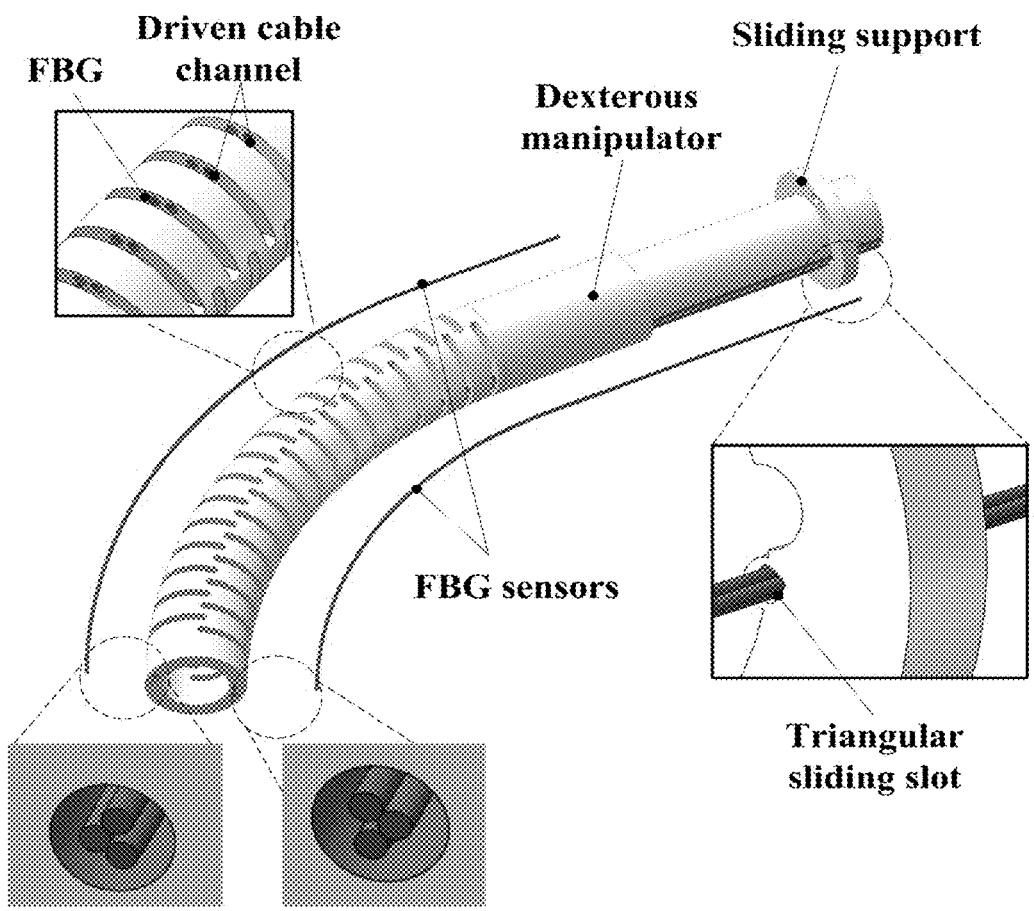
FIG. 5 illustrates shape sensing for an osteolysis dexterous manipulator.

The DCM can bend in the plane as shown in FIG. 5. The bending modulus in this plane is much larger than that of other planes. Therefore, 2D shape sensing is sufficient to track the position of the DCM. FIG. 5 shows the overall design, in which two SSAs are inserted through the channels within the DCM wall. At the distal end of the DCM, the SSAs are attached to the DCM body keeping their neutral plane perpendicular to the bending plane. At the proximal end, there is a sliding support with tiny triangular holes in it, through which the SSA will be inserted. The embodiments of the invention are not limited to 2D shape sensing. For example, the same methods could be applied for sensing 3D shapes if DCM is built to accept 3D bending, i.e, bending in two perpendicular planes but not twisting. The method and system for 2D sensing can be extended to 3D sensing by using three sensing units at 120 degrees instead of 2 sensing units at 180 degrees. Additional sensors could also be used for redundancy.

The design features of the DCM sensors are shown in FIG. 5 and described in the following:

(a) The DCM has an inner lumen for the surgical instruments, such as a curettage, a cutter, or a brush to get through. This lumen cannot be occupied by sensors since they may interfere with those instruments. Also, we cannot place the sensors on the outer surface of the DCM since that increases its overall size. Therefore the sensor is inserted in the channels through the wall of the DCM.

(b) The SSA can freely move along the DCM. A single sensor on one side of the DCM is either in tension or compression. This will result in a biased length for the sensor. By using two SSAs in opposite sides, we can compensate for the changes in lengths due to tension and compression effects.

(c) The twisting of the SSA will affect the results of shape sensing to a great extent [18]. Since the SSAs are flexible, they can easily twist as the DCM bends. To prevent torsion, a sliding support was added to the proximal end of the DCM. This, together with the non-uniform bending modulus of the SSA will prevent the sensor from twisting.

(d) The DCM is a segmented structure. The nitinol fibers allow the SSA to maintain a continuous curvature through the DCM channels in order to prevent the FBG fiber from breaking.

To develop a theoretical model for the SSA, it is necessary to find its neutral plane. We assume the SSA is a composite beam with a different material at each section. The neutral plane can be obtained from the equilibrium equation of forces:

$$\int_{A_1} \sigma_1 dA_1 + 2\int_{A_2} \sigma_2 dA_2 = F_N = 0 \quad (3)$$

$$\sigma_i = E_i(y - \Delta)/\rho$$

where $\sigma_i$ and $E_i$ (i=1, 2) are the stress and Young's modulus for optical fiber and nitinol wire. We can also find the location of neutral plane:

$$\Delta = \frac{2E_2 D_2^2 t}{\{E_1 D_1^2 + 2E_2 D_2^2\}}, t \in \left[\frac{d_{core}}{2}, \frac{\sqrt{(D_1 + D_2)^2 - D_2^2}}{2}\right] \quad (4)$$

where $d_{core}$ is the radius of the optical fiber core and $D_i$ (i=1,2) are the outer diameter of the optical fiber and nitinol wire.

The triangular structure of the SSA leads to a different bending modulus for each side. This causes the SSA to bend only in the direction of smallest bending modulus.

The equivalent bending modulus can be obtained from equilibrium equation for bending moment on the cross section of SSA:

$$\int_{A_1} y\sigma_1 dA_1 + \int_{A_2} y\sigma_2 dA_2 = M \quad (5)$$

The location of the neutral plane is:

$$\Delta = \frac{E_2 D_2^2 (y_1' + y_2')}{E_1 D_1^2 + 2E_2 D_2^2} \quad (6)$$

where $y'_1$ and $y'_2$ are the coordinates for nitinol wires after rotating a certain angle.

Then, the equivalent bending modules can be written as:

$$W_e = E_1 I_1 + E_2 I_2 + E_3 I_3 \quad (7)$$

$$= E_1\left(I_{10} + \frac{\Delta^2 \pi D_1^2}{4}\right) +$$
$$E_2\left(2I_{20} + \frac{(y_1' - \Delta)^2 \pi D_2^2}{4} + \frac{(y_2' - \Delta)^2 \pi D_2^2}{4}\right)$$

where $I_{i0} = D_i^2/64$ (i=1, 2) is the moment of inertia for the optical fiber and nitinol wire.

Table 2 shows the properties and dimensions of the material used in the SSA (see FIG. 3).

TABLE 2

| Material properties and dimensions | |
| --- | --- |
| FBG optical fiber | |
| Young's modulus | 70 GPa |
| Outer diameter | 100 µm |
| Nitinol wires | |
| Young's modulus | 75 GPa |
| Outer diameter | 125 µm |
| Assembly | |
| t | 80 µm |

Figure 6:
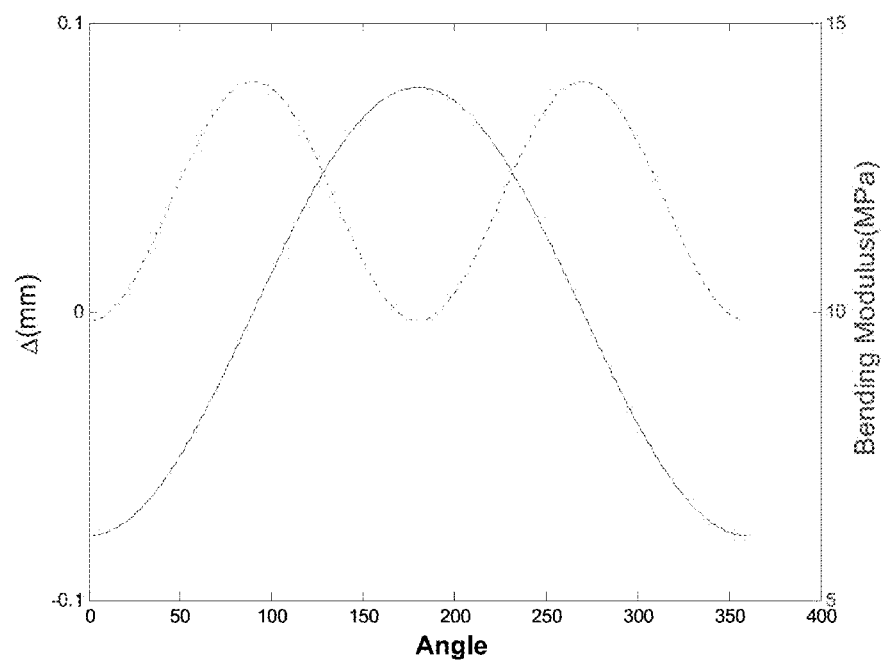
FIG. 6 shows Δ and equivalent bending modulus in 360° bending orientation.

With these parameters, we can calculate the position of the neutral plane, A, and the equivalent bending modulus in 360 bending orientation (FIG. 6). The maximum difference in directional bending modulus was found to be 20 MPa. To increase this value, we can reduce the distance between the centers of fiber and nitinol wires. Therefore, using this triangular structure, we can meet both requirements of reducing the working wavelength range and creating an non-uniform bending modulus.

Twisting is a common problem in the design of shape sensors. Some researchers have reduced this effect by using anti-twisting structures such as the braided polymer tube [19]. In our design, we have used a ring with triangular holes to keep the SSA from twisting. This ring maintains the orientation of the SSA at the proximal end.

Figure 7:
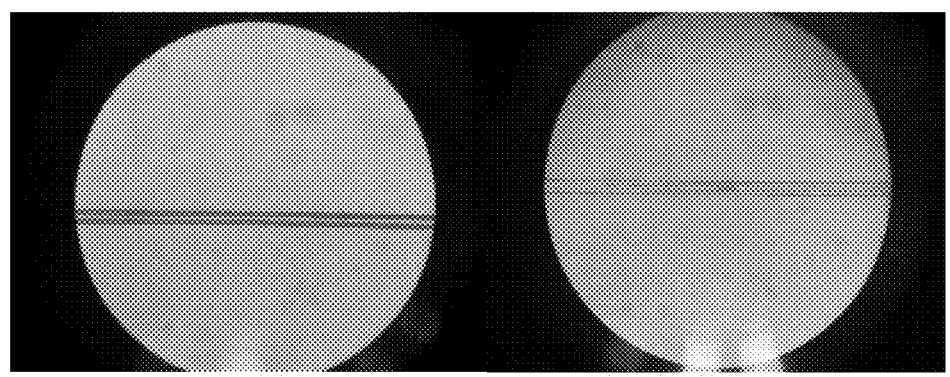
FIG. 7 shows the shape sensor array (SSA) parallel nitinol wires (left) and Fiber Bragg grating (FBG) fiber (right) under a microscope.

The optical fiber used in this study contains an array of three FBG sensors distributed 10 mm apart. The length of the active area for each sensor is 3 mm (Technica SA, China). LOCTITE 3101, a modified acrylate UV glue (Henkel, Germany) was used to glue two nitinol wires with oxide surface (NDC Technologies, USA) to the FBG optical fiber. An assembly device was designed to precisely maintain the relative position between the optical fiber and these wires. FIG. 7 shows the SSA assembly under microscope (ZEISS, Germany) at 25 times magnification. After the assembly, the SSA was placed inside the DCM wall channels. The optical fiber was fixed at the distal end, and a triangular slot was manufactured by laser cutting (Laserage Technology Corporation, USA) to maintain its orientation at the proximal end. While specific values for the sensor dimensions and positions are provided herein, these value are purely exemplary, and the embodiments of the invention are not limited to these values.

Figure 8:
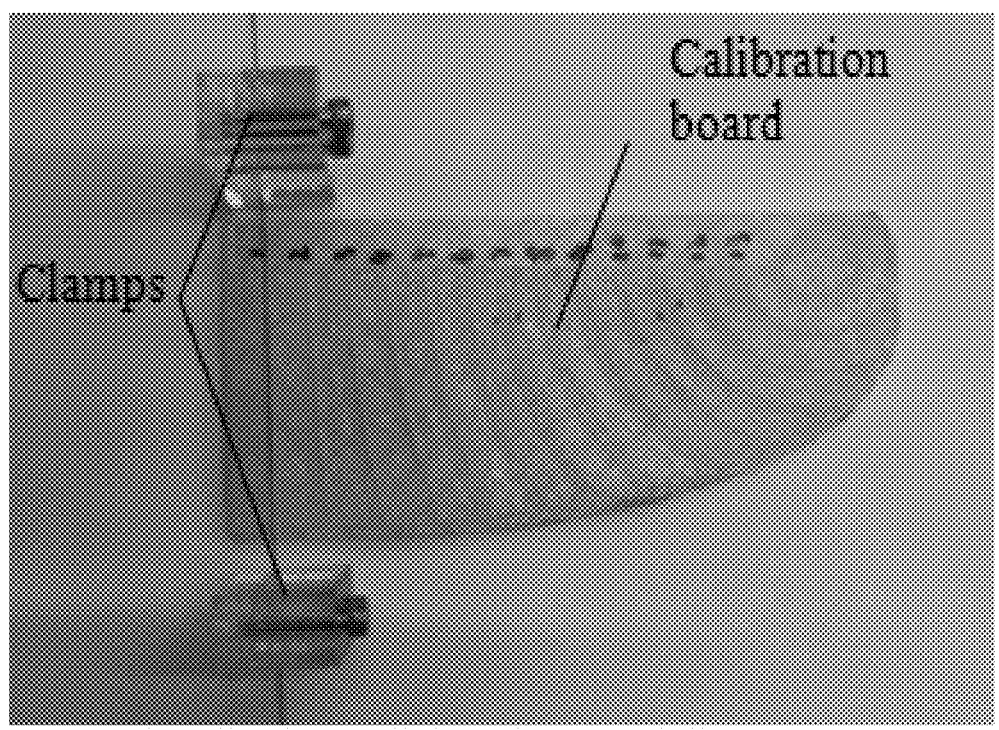
FIG. 8 shows a calibration board for a 2D shape sensor array.
Figure 9:
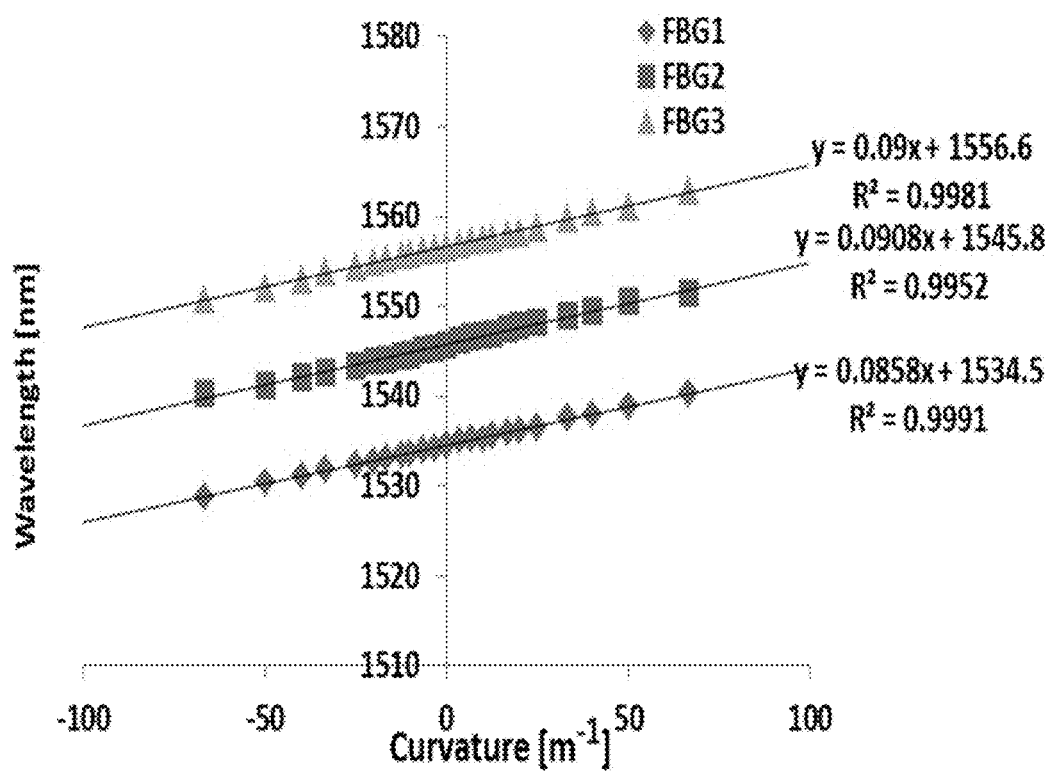
FIG. 9 shows calibration results for an array of three FBG sensors.

To validate the linearity of the curvature-wavelength relationship, a multi-channel calibration board with different curvatures was designed and 3D printed, and is shown in FIG. 8. For this experiment, two clamps with triangular slots were fabricated to preserve the orientation of the SSA on both sides. FIG. 9 illustrates the results of calibration for all three sensors within the SSA. The slopes of the fitting lines are slightly different. This may be due to the precision of the assembly or the use of a varying amount of glue.

The wavelength range for each FBG sensor, and the number of FBG sensors that we can use are limited due to the wavelength range of the interrogator. In this case, within the 40 nm wavelength range of the interrogator (Micron Optics, Inc. USA), three FBG sensors were placed along the optical fiber.

For the 2D shape reconstruction, we assumed a linear relationship between curvature and the arc length. We calculated the tangent angle, θ, from curvature, ρ, using the equations shown below:

$$\theta(s) = \int_0^s \rho(s)\,ds + \theta_0 \quad (8)$$

$$\begin{cases} x = \int_0^s \cos\theta\,ds \\ y = \int_0^s \sin\theta\,ds \end{cases} \quad (9)$$

Figure 10:
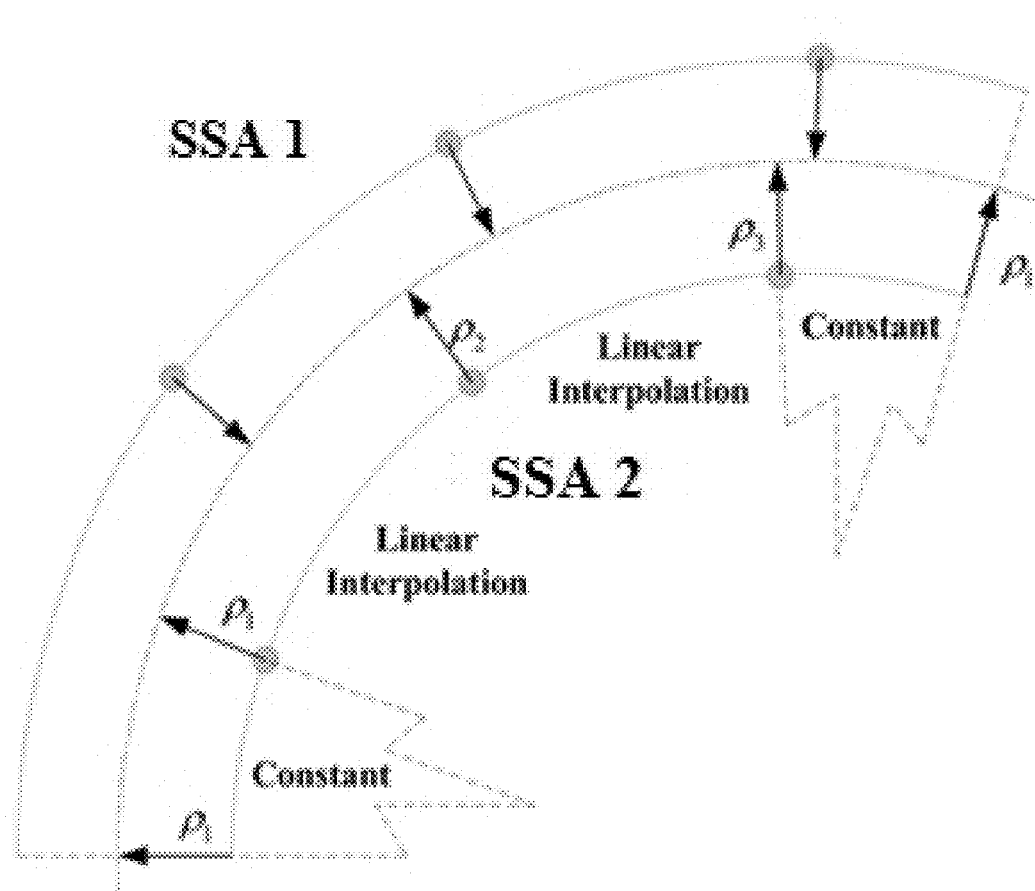
FIG. 10 shows an arrangement of FBG sensors for shape reconstruction.

FIG. 10 shows the arrangement of the FBG sensors (six circles) on SSA along the DCM. When the DCM bends, the arc length for the side where SSA 1 is located increases and the three FBG sensors cannot cover the whole length of the DCM. On the other hand, the arc length for the side where SSA 2 is located decreases and its three FBG sensors can cover the arc length. When the DCM bends towards the opposite side, the opposite is true about these sensors. Therefore, the two SSAs are highly complementary and by using the combination of their data, we can construct the 2D shape for the DCM's centerline.

Figure 11:
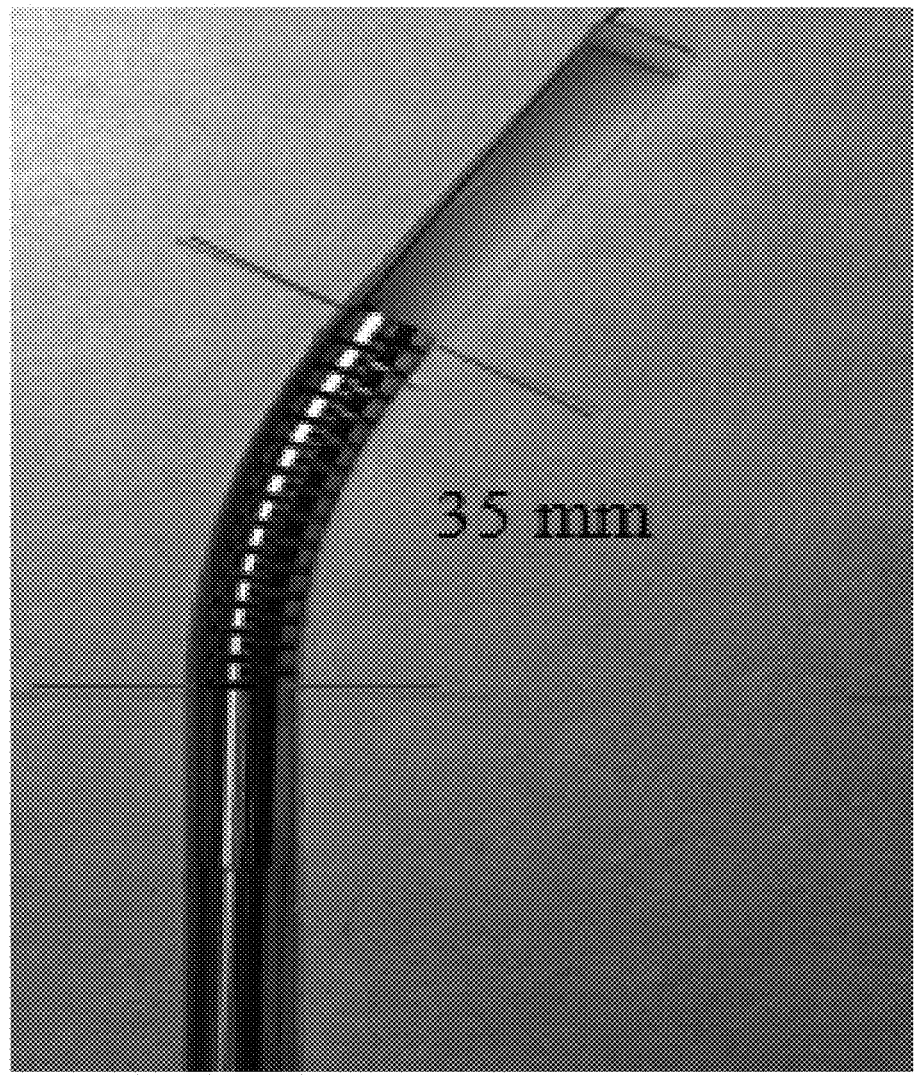
FIG. 11 shows FBG calibration using constant curvatures.

For reconstructing the shape of the DCM in real-time, we first found the wavelength-curvature relationship for SSA inside the channels within the walls of the DCM. For this purpose, we designed and manufactured a calibration board that contained five slots with different curvatures, ranging from 15.6 m$^{-1}$ to 50.8 m$^{-1}$. These slots were built according to the dimensions of the DCM (6 mm outer diameter and 35 mm length) such that it could fix the position of the DCM within a constant curvature. During the experiments, the optical fiber was kept under tension using a 7.6 grams weight. The DCM was manually placed in the slots and wavelength data were recorded for all of the FBG sensors. This process was repeated 10 times for each slot. FIG. 11 shows the constant curvature bending of the DCM inside the slot. Since the curvature was constant, the wavelength shifts for all of the FBG sensors within SSA were expected to be the same.

For a preliminary verification of our proposed method, we generated the calibration curve from wavelength data obtained from four of the slots at each time. The wavelength data from the fifth slot was then used for predicting the curvature of that slot (leave-one-out experiments). The leave-one-out verification experiments were performed for the three middle slots. The mean error was found to be 2.9% for the 23.8 m$^{-1}$ curvature, 4.4% for 32.4 m$^{-1}$ curvature, and 3.8% for 41.4 m$^{-1}$ curvature. FIG. 12 shows the mean wavelength shift of the FBG sensors for different curvatures. In this case, the verification was done for the slot with a 33.4 m$^{-1}$ curvature.

We described herein a novel shape sensor for the DCM. For this purpose, we used FBG fibers along with nitinol wires as the supporting substrate to form a triangular cross section. The neutral plane of the SSA assembly was adjusted to reduce the wavelength shift of the FBG sensors. In addition, the bending modulus was kept non-uniform causing the SSA bend in the same direction as the DCM. The calibration curves showed a fairly linear curvature-wavelength relationship for SSA sensors. For verification, we assembled the SSA within the wall of the DCM and performed leave-one-out experiments. Experimental results indicate that the SSA can detect the DCM's curvature with an error of less than 4.4%.

References—Example 1

[1] P. Sears and P. E. Dupont, "Inverse kinematics of concentric tube steerable needles," in Robotics and Automation, 2007 IEEE International Conference on, pp. 1887-1892, 2007.

[2] R. J. Webster, J. M. Romano and N. J. Cowan, "Mechanics of precurved-tube continuum robots," Robotics, IEEE Transactions On, vol. 25, pp. 67-78, 2009.

[3] D. Reynaerts, J. Peirs and H. Van Brussel, "Shape memory micro-actuation for a gastro-intestinal intervention system," Sensors and Actuators A: Physical, vol. 77, pp. 157-166, 1999.

[4] K. Ikuta, K. Yamamoto and K. Sasaki, "Development of remote microsurgery robot and new surgical procedure for deep and narrow space," in Robotics and Automation, 2003. Proceedings. ICRA'03. IEEE International Conference on, pp. 1103-1108, 2003.

[5] D. B. Camarillo, C. F. Milne, C. R. Carlson, M. R. Zinn and J. K. Salisbury, "Mechanics modeling of tendon-driven continuum manipulators," Robotics, IEEE Transactions On, vol. 24, pp. 1262-1273, 2008.

[6] N. Simaan, R. Taylor and P. Flint, "High dexterity snake-like robotic slaves for minimally invasive telesurgery of the upper airway," in Medical Image Computing and Computer-Assisted Intervention-MICCAI 2004, Springer, 2004, pp. 17-24.

[7] M. D. M. Kutzer, S. M. Segreti, C. Y. Brown, M. Armand, R. H. Taylor and S. C. Mears, "Design of a new cable-driven manipulator with a large open lumen: Preliminary applications in the minimally-invasive removal of osteolysis," in Robotics and Automation (ICRA), 2011 IEEE International Conference on, pp. 2913-2920, 2011.

[8] S. M. Segreti, M. D. M. Kutzer, R. J. Murphy and M. Armand, "Cable length estimation for a compliant surgical manipulator," in Robotics and Automation (ICRA), 2012 IEEE International Conference on, pp. 701-708, 2012.

[9] R. J. Murphy, M. D. Kutzer, S. M. Segreti, B. C. Lucas and M. Armand, "Design and kinematic characterization of a surgical manipulator with a focus on treating osteolysis," Robotica, pp. 1-16, 2013.

[10] Y. Otake, J. Stayman, W. Zbijewski, R. Murphy, M. Kutzer, R. Taylor, J. Siewerdsen and M. Armand, "Model-based cone-beam CT reconstruction for image-guided minimally invasive treatment of hip osteolysis," in SPIE Medical Imaging, pp. 86710Y-86710Y-7, 2013.

[11] A. M. Franz, T. Haidegger, W. Birkfellner, K. Cleary, T. M. Peters and L. Maier-Hein, "Electromagnetic Tracking in Medicine—a Review of Technology, Validation and Applications," 2014.

[12] Y. Park, S. Elayaperumal, B. Daniel, S. C. Ryu, M. Shin, J. Savall, R. J. Black, B. Moslehi and M. R. Cutkosky, "Real-time estimation of 3-D needle shape and deflection for MRI-guided interventions," Mechatronics, IEEE/ASME Transactions On, vol. 15, pp. 906-915, 2010.

[13] W. N. MacPherson, M. Silva-Lopez, J. S. Barton, A. Moore, J. Jones, D. Zhao, L. Zhang, I. Bennion, N. Metje and D. Chapman, "Tunnel monitoring using multicore fibre displacement sensor," Measurement Science and Technology, vol. 17, pp. 1180, 2006.

[14] X. F. Chen, C. Zhang, D. J. Webb, K. Kalli and P. Gang-Ding, "Highly sensitive bend sensor based on Bragg grating in eccentric core polymer fiber," IEEE Photonics Technology Letters, vol. 22, pp. 850-852, 2010.

[15] F. Araújo, L. Ferreira, J. Santos and F. Farahi, "Temperature and strain insensitive bending measurements with D-type fibre Bragg gratings," Measurement Science and Technology, vol. 12, pp. 829, 2001.

[16] X. Yi, J. Qian, L. Shen, Y. Zhang and Z. Zhang, "An innovative 3D colonoscope shape sensing sensor based on FBG sensor array," in Information Acquisition, 2007. ICIA'07. International Conference on, pp. 227-232, 2007.

[17] R. J. Roesthuis, M. Kemp, van den Dobbelsteen, John J and S. Misra, "Three-dimensional needle shape reconstruction using an array of fiber bragg grating sensors," 2013.

[18] J. P. Moore and M. D. Rogge, "Shape sensing using multi-core fiber optic cable and parametric curve solutions," Optics Express, vol. 20, pp. 2967-2973, 2012.

[19] Seok Chang Ryu, Pierre E. Dupont, "FBG-based Shape Sensing Tubes for Continuum Robots," IEEE International Conference on Robotics & Automation (ICRA), pp. 3531-3537, May 31-Jun. 7, 2014. 2014.

Example 2

Shape Tracking of a Dexterous Continuum Manipulator Utilizing Two Large Deflection Shape Sensors Dexterous continuum manipulators are commonly used in minimally invasive surgery (MIS) due to their superior steerability and large operating space. Previous studies have proposed and tested variations of surgical DCMs for robotic minimally invasive surgery [1, 2]. We have developed a cable-driven DCM for the treatment of osteolysis (FIG. 13A). The DCM removes and replaces osteolytic lesions occurring as a result of joint wear after total hip arthroplasty [3]. This MIS approach uses the screw holes of a well-fixed acetabular implant to reach an osteolytic lesion without removing the well-fixed implant, as shown in FIG. 13B. We believe that using the DCM will enable surgeons to access nearly the entire osteolytic lesion [4] compared to the reported 50% from rigid tools [5]. However, there is still no effective intraoperative technique for shape sensing when applying DCM. Previous efforts involved developing models for estimating the shape from cable-length measurements [6] as well as the intermittent use of x-ray for updating the model estimation [7]. However, the predictive model met with limited success, even without considering the unknown interaction with tissue and bone. Additionally, the amount of radiation exposure to the patient precludes real-time x-ray control.

Multi-strain sensors are capable of detecting curvatures of multiple points along the DCM, enabling reconstruction of the DCM shape. Polymer strain sensors, such as piezoelectric and piezoresistive polymers, are competitive for large deflection shape sensing, as they yield to large strains. Cianchetti et al. used Electrolycra, a piezoresistive sensor of 10 mm×15 mm to reconstruct the spatial configuration of a 2D DCM, OCTOPUS, which is able to bear a strain up to 60% [8]. Shapiro et al. utilized polyvinylidene fluoride (PVDF), a thin 25 mm×13 mm piezoelectric polymer to build the 2D shape of a hyper-flexible beam [9]. However, the stress-strain hysteresis of the piezoresistive polymer and the bias and drifting problem of PVDF bring in considerable errors and difficulties to the signal processing. Moreover, PVDF's size and requirement for multiple lead wires are not compatible with a micro surgical DCM.

The FBG sensor is another commonly used strain sensor, offering a great number of advantages over polymer type sensors. These include electromagnetic interferences (EMI) immunity, stability, repeatability, high sensitivity and fast response. Moreover, multi-sensing nodes can be contained within one optical fiber, allowing all sensing nodes to share one connector. Due to their intrinsic characteristics, FBG sensors are particularly well suited for precisely measuring strain for shape tracking.

Various types of curvature detecting sensors based on FBGs have already been devised. Yi et al. evenly attached four multi-FBGs optical wires to a 0.76 mm NiTi wire and used it to detect the shape of a colonscope [10]. Park et al. developed a 3D shape sensor for MRI-compatible biopsy needles by creating three 350 um grooves along the 1 mm diameter inner stylet and embedded three FBG optical fibers in these slots [11]. Roesthuis et al. used a similar method, but utilized a 1 mm diameter NiTi needle [12]. Other ways to achieve directional bend sensitivity in FBG-based solutions include employing fibers with asymmetrical core or cladding geometries, introducing an asymmetrical index perturbation in the cross section of fiber by the use of CO or femtosecond lasers, such as the multi-core fiber [13], eccentric core fiber [14], and D-shape sensor [15]. Moore used multi-core fiber with FBG arrays for 3D shape sensing [16]. A multi-core FBG can detect larger curvature than previous kinds, but each fiber core must be separated sufficiently to avoid core-core interaction. Similar to multi-core fiber, Moon et al. assembled three FBG optical fibers in a triangular shape molded with epoxy [17]. Among all previous work, the maximum curvature detected was 22.7 $m^{-1}$ [12]. Our DCM is capable of an extremely tight radius of curvature (approximately 6 mm), resulting in an approximate curvature of 166.7 $m^{-1}$ [6]. Current shape or curvature sensors have been unable to detect such a large curvature.

Generally, curvature detection is the basis of shape tracking. An array of FBG sensing nodes are placed along an optical fiber and the fiber's shape is reconstructed from the curvatures detected by each sensing node. The FBG sensing node detects curvature based on the wavelength change of FBG due to strain and the thermal effect on wavelength. According to He, et al. [19], the wavelength shift $\Delta\lambda$ is:

$$\Delta\lambda = \kappa_\varepsilon \cdot \varepsilon + \kappa_{\Delta T} \cdot \Delta T \qquad (10)$$

where $\kappa_\varepsilon$ is the strain coefficient, $\kappa_{\Delta T}$ is thermal coefficient, $\varepsilon$ is strain, T is temperature and $\Delta$ stands for the increment of a specific variable.

The FBG optical fiber is attached to a substrate; therefore, the curvature of the core of the FBG optical fiber is biased from the neutral bending plane of the overall assembly. The curvature is proportional to the strain that the FBG core undertakes. If the temperature influence is well compensated, the curvature is proportional to the wavelength shift, $$\kappa = \frac{\Delta\lambda}{k_\varepsilon \cdot \delta} \qquad (11)$$

where κ denotes the curvature and δ denotes the biased distance of FBG core from the neutral plane.

Figure 14:
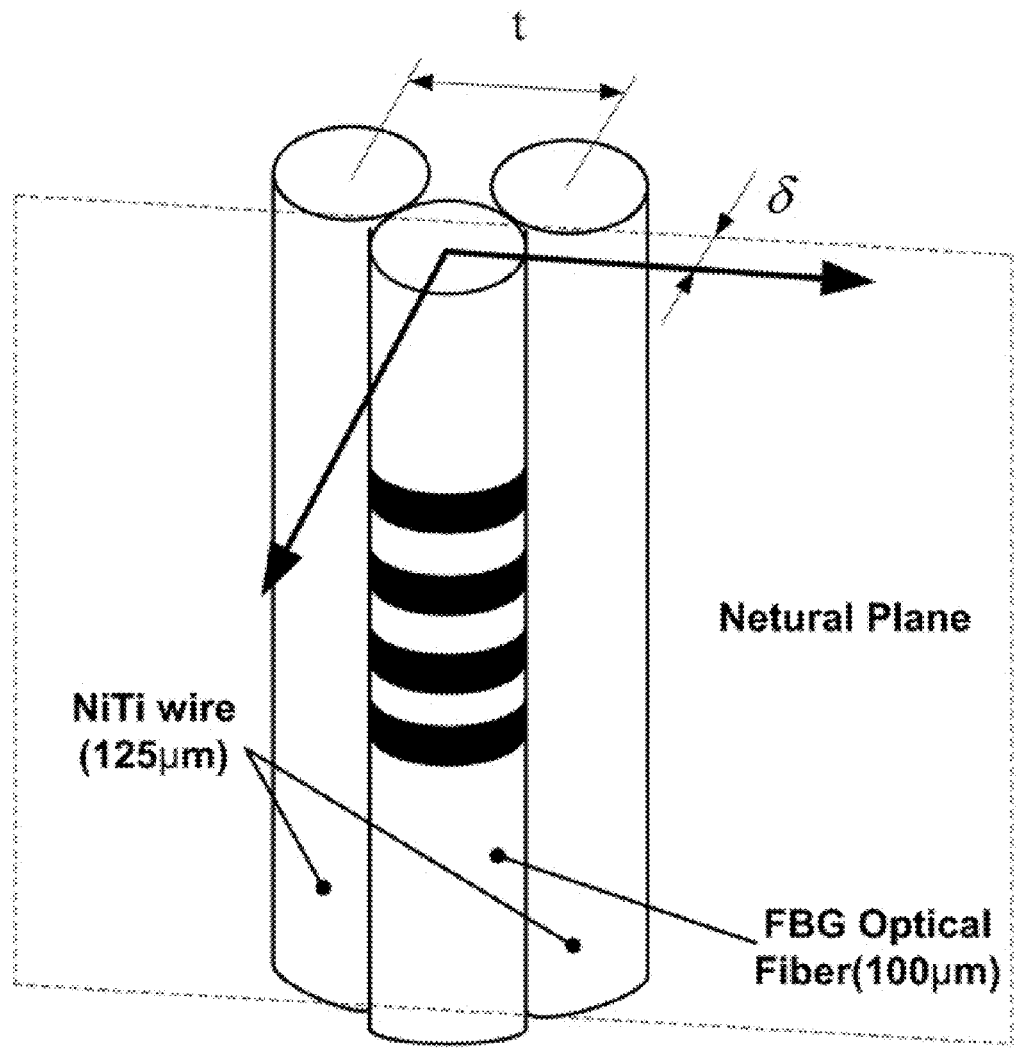
FIG. 14 shows a configuration of a large curvature detection sensor.

FIG. 14 shows the configuration of our large curvature detecting sensor, which includes one FBG optical fiber and two NiTi wires in parallel as substrate. The biased distance from the neutral plane allows the FBG to detect large curvature without exceeding its breaking strain of 0.5% [20]. The strain sensitivity of our curvature sensor is adjusted by controlling the distance, t, between the two NiTi wires. A larger t generates a smaller δ, which enables the sensor to detect larger curvature. Additionally, the bending modulus varies in the circumferential direction, which gives the sensor tendency to bend in a specific direction. To a certain extent, this restricts the sensor from twisting.

To detect the shape, multi curvature sensors are needed. Herein, each curvature sensor is called the shape sensing node. Also, the assembly of FBG arrays with NiTi wires is called a shape sensor.

Figure 15A:
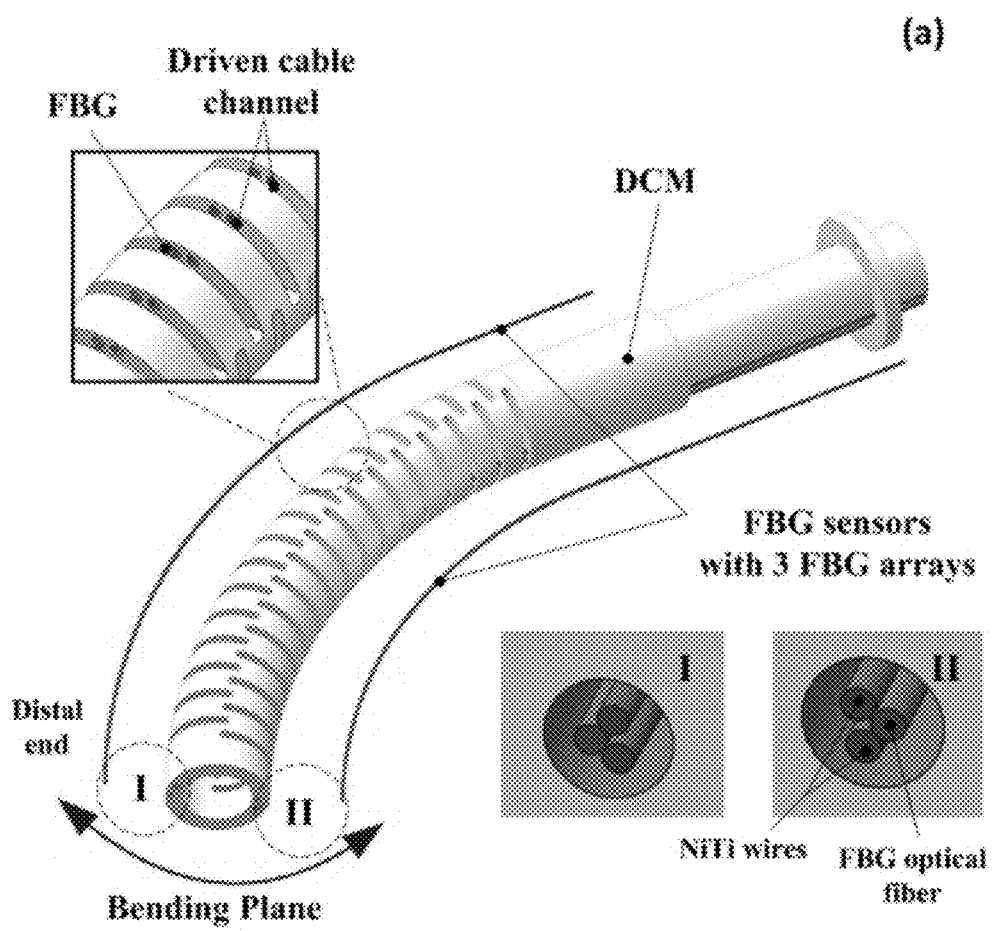
FIG. 15A shows an assembly of shape sensors for the DCM.

Our DCM is a nested NiTi tube cut with notches and has two drive cables actuating a planar bend for a 35 mm bending segment. Since the bending is limited to two inflection points along the length of the DCM, we have used two shape sensors with three FBG sensing nodes for DCM shape tracking. FIG. 15A shows the assembly of the shape sensors onto the DCM. The sensors pass through channels within the walls of the DCM, and the distal ends are fixed. The sensors' neutral planes are kept perpendicular to the bending plane of the DCM. The sensors are able to move freely within the channels as the DCM bends and straightens. This allows the FBG sensing nodes on the tension side to move forward to the DCM distal tip, while the FBG sensing nodes on the contracting side will move backward to the proximal end. If only one shape sensor is used, there may be a significant segment without FBG sensors in the proximal part of the bending segment when the DCM bends too much. Two shape sensors in both sides will allow better coverage of the full DCM shape. In order to more accurately capture the shape of the DCM, the desired scheme is to assemble two shape sensors within each side of the DCM. Additionally, two shape sensors may help to eliminate any temperature gradient influence on the FBG's wavelength.

Figure 15B:
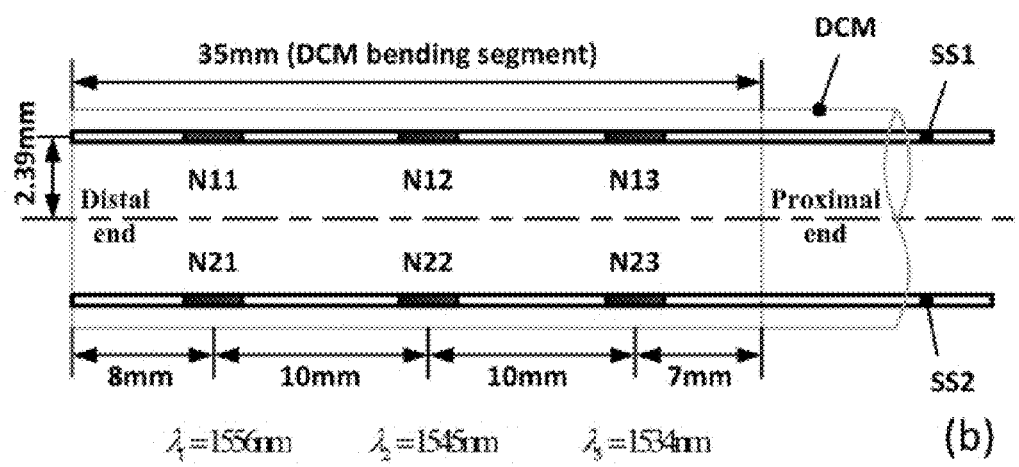
FIG. 15B shows an arrangement of FBG sensing nodes.

FIG. 15B shows the detailed arrangement of the FBG sensing nodes along the shape sensor, and the assembly of the sensors to the DCM. The sensors' lumens are located along the wall of the manipulator and 2.39 mm from the DCM's centerline. Three 3 mm length FBG sensing nodes were arranged 10 mm apart. The magnitude of curvature change resulting from the bend of the DCM is unknown; therefore the sensing nodes are evenly spaced along the sensor. The sensing nodes N11 and N21 are 8 mm from the distal end (the tip of DCM) to avoid placing the sensor within the rigid part of DCM with no notches. The sensing nodes N13 and N23 are 7 mm from the proximal end (the base of DCM) to keep the sensor within the bending segment. The wavelengths of the three FBG sensing nodes are 1534 nm, 1545 nm, and 1556 nm. These were selected by considering the 40 nm wavelength detection range of the interrogator used for data acquisition. Each of the sensing nodes uses a 14 nm wavelength range to allow for large curvature detection.

The relationship between wavelength shift and curvature for the FBG sensing nodes was calibrated according to [17]. A curvature matrix was obtained from a series of known constant curve slots and the wavelength shift for each of them.

The shape sensor curves may be reconstructed using measured curvatures along the shape sensor. For the 2D case with our DCM, we only considered planar bending. Several discrete curvature points are measured and further extended to the whole length of the sensor. As shown in (12), a linear relationship between curvature and arc length is assumed. This simple relationship keeps the curvature continuous, the shape smooth, and reduces computational complexity. In a Cartesian coordinate system, the tangent angle of point with respect to the X axis is obtained from (13), and the coordinates for a series of discrete points can be obtained from (14).

$$\kappa = a \cdot s + b \quad (12)$$

$$\theta(s) = \int_0^s \kappa(s)\,ds + \theta_0 \quad (13)$$

$$\begin{cases} \Delta x = \cos\theta \Delta s \\ \Delta y = \sin\theta \Delta s \end{cases} \quad (14)$$

where a and b denote coefficients for linear interpolation for curvature and s denotes the arc length.

The DCM's shape is reconstructed according to the following six steps, and highlighted in FIGS. 16A-16F. While the embodiments below describe shape detection using FBG arrays, the method can also be applied to other detectors, for example strain gage detectors. According to some embodiments, a metal wire with regular strain gages on it may replace the optical fiber, and may be used with nitinol wires as described herein for the optical fiber.

Figures 16A, 16B, 16C, 16D, 16E, 16F:
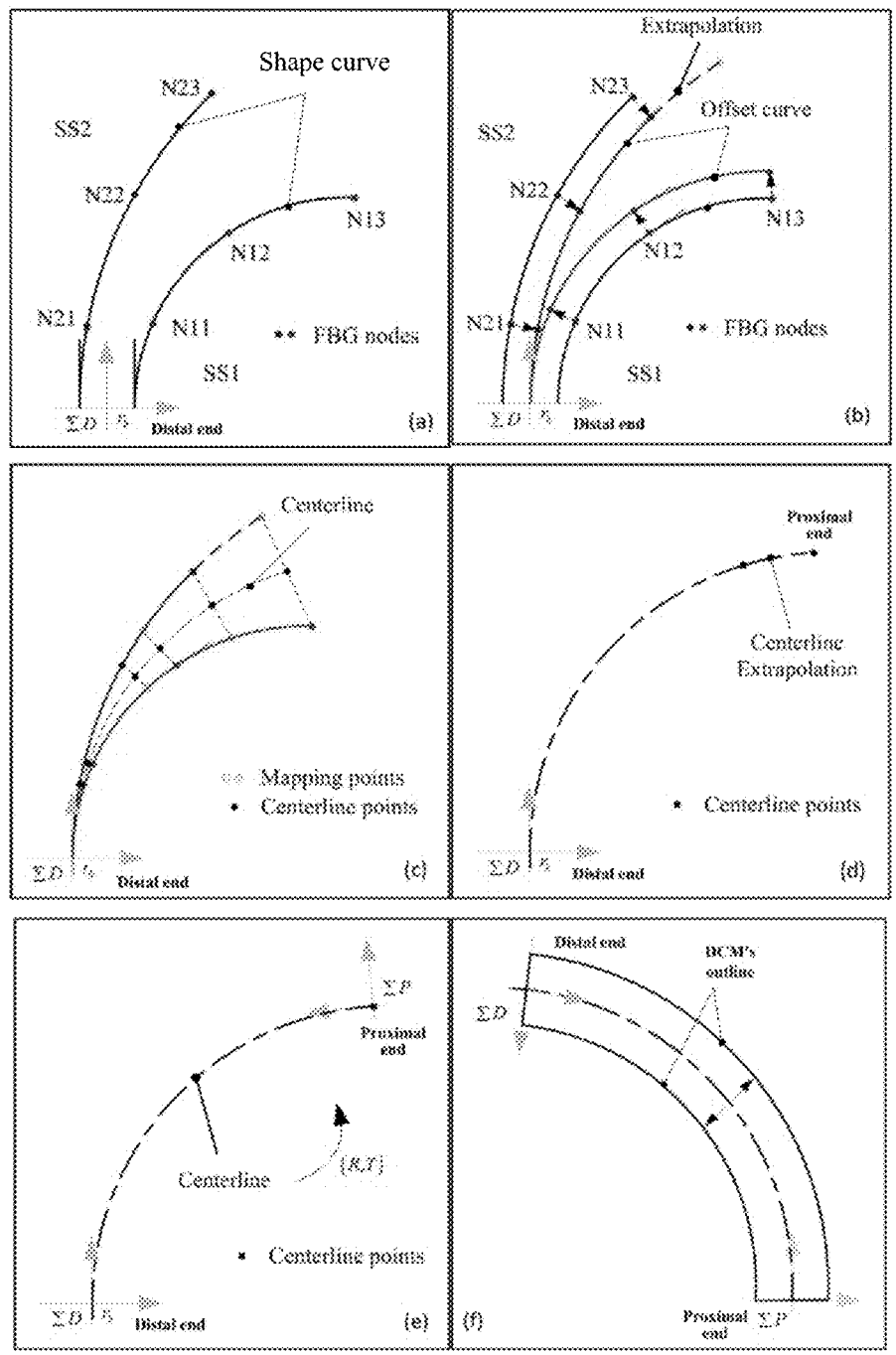
FIG. 16A illustrates step 1 of the shape reconstruction method: starting from the distal end, calculate the shape curves of both sensors using the method described above, and keep the distance between start points and the tangential direction of two shape sensor curves (SS1 and SS2) $2r_b$, and parallel ($\pi/2$ herein)
FIG. 16B illustrates step 2: offset two sensor curves to the centerline of the DCM.
FIG. 16C illustrates step 3: extrapolate two offset curves to obtain two curves with the same length, and then calculate their centerline.
FIG. 16D illustrates step 4: extrapolate the centerline to be 35 mm long which represents the DCM centerline.
FIG. 16E illustrates step 5: calculate the tangential direction of the proximal end, build the proximal coordinate system ΣP, and calculate the transformation matrix.
FIG. 16F illustrates step 6: transform the reconstructed centerline and offset the centerline to get the DCM's outline.

Step 1: Starting from the distal end, calculate the shape curves of both sensors using the method described above, and keep the distance between start points and the tangential direction of two shape sensor curves (SS1 and SS2) $2r_b$, and parallel ($\pi/2$ herein), as shown in FIG. 16A. It is difficult to reconstruct the shape curve from the proximal end because the FBG sensing nodes near the proximal end move during DCM bending. However, it is feasible to build the shape starting from the distal end, because the distances from all FBG sensing nodes to the distal end remains constant. Herein, ΣD represents the coordinate system built with the center of the distal end as the origin point. The distance between each of the shape sensors and DCM's centerline, $r_b$, is a constant; this enforces a correct outline of the DCM. FBG sensing nodes N11 and N21 on two shape sensors are a certain length away from the distal end for detecting an effective curvature. The distal end curvatures of the two shape sensors are set to be the same as that of N11 and N21.

Step 2: offset two sensor curves to the centerline of the DCM, as shown in FIG. 16B. The points' coordinates on each offset curve can be obtained by $$\begin{bmatrix} x_o \\ y_o \end{bmatrix} = \begin{bmatrix} x_{ss} \\ y_{ss} \end{bmatrix} + \begin{bmatrix} \sin\theta \\ -\cos\theta \end{bmatrix} \cdot r_b \cdot \frac{\kappa}{|\kappa|} \quad (15)$$

where $x_0$ and $y_0$ denote the coordinates of points on the offset curves, $x_{ss}$ and $y_{ss}$ denote the coordinates of points on the shape curves, and θ and κ denote the tangential angle with respect to x axis of ΣD and curvature of a point.

Ideally, the two sensors' curves should coincide with each other in the distal part after offsetting, but due to errors caused by factors such as friction between the shape sensor and its lumen through the DCM wall and temperature variation, two separate offset curves are obtained.

Step 3: extrapolate two offset curves to obtain two curves with the same length, as shown in FIG. 16B, and then calculate their centerline, as shown in FIG. 16C. The length of shape curves are different after offsetting, therefore, the shape curve of the shorter curve is extrapolated. With two point sets, the nearest point pairs from both sides are searched and the middle points are calculated to represent the DCM's centerline.

Step 4: extrapolate the centerline to be equal to the distance from the proximal to the distal end of the DCM. In the example, the length is 35 mm, but other length DCMs can be used. The extrapolated centerline represents the DCM centerline, as shown in FIG. 16D.

Step 5: calculate the tangential direction of the proximal end, build the proximal coordinate system ΣP, and calculate the transformation matrix as shown in FIG. 16E.

Step 6: transform the reconstructed centerline and offset the centerline to get the DCM's outline, as shown in FIG. 16F. By offsetting said centerline in each of at least two opposing directions substantially orthogonal to the centerline by a predetermined amount, one can determine a two dimensional or three dimensional calculated outline of the DCM.

The coordinates can be calculated by, $$\begin{bmatrix} x \\ y \end{bmatrix}_{\Sigma P} = \begin{bmatrix} \cos\theta_{cd} & \sin\theta_{cd} \\ -\sin\theta_{cd} & \cos\theta_{cd} \end{bmatrix}_{\Sigma D} \left( \begin{bmatrix} x \\ y \end{bmatrix}_{\Sigma P} - \begin{bmatrix} x_{cd} \\ y_{cd} \end{bmatrix}_{\Sigma D} \right) \quad (16)$$

where x and y denote the coordinates of a point, $\theta_{cd}$ denotes the tangential angle of the distal point, $x_d$ and $y_d$ denote the coordinates of the distal point, and the subscripts ΣD and ΣP denote the coordinate systems.

Figure 17A:
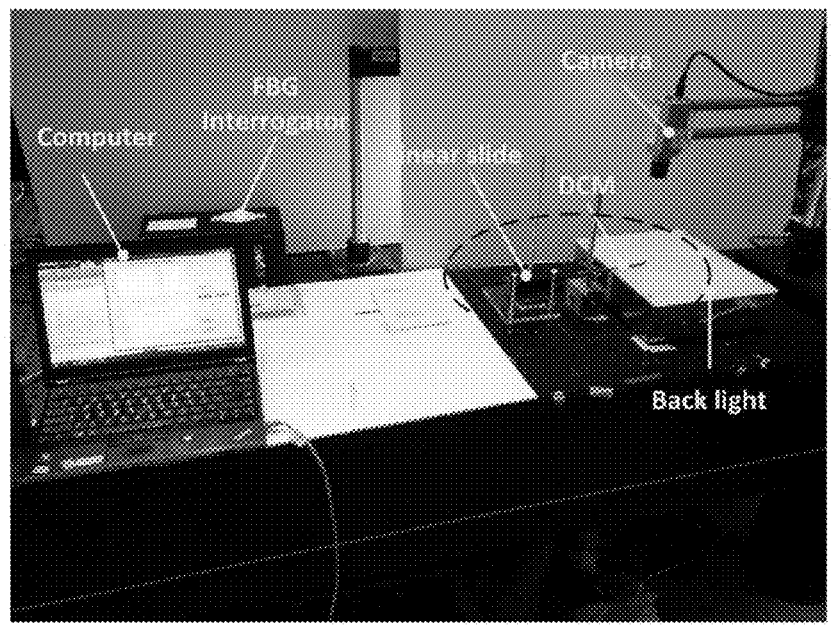
FIG. 17A shows a view of the experimental platform according to some embodiments.
Figure 17B:
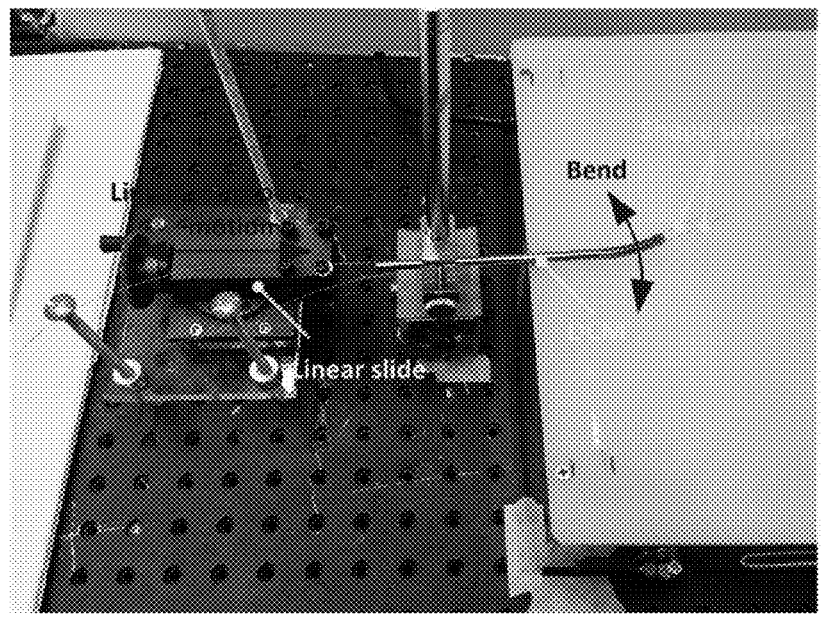
FIG. 17B shows an enlarged view of the area in the dashed oval in FIG. 17A.

Experiments were performed to estimate the shape reconstruction performance of the above shape tracking scheme. FIGS. 17A and 17B show the experimental setup. Two sets of experiments were carried out: 1) free bending, and 2) bending in presence of obstacles on the path.

The reflective wavelengths from the FBG shape sensors (Technica Optical Components, China) were analyzed using a Micron Interrogator (Micron Optics, USA). The wavelengths were processed and the reconstructed shape was displayed with algorithms written in MATLAB (MathWorks, USA). A PL-B741 camera (PixeLink, USA) was used to capture planar images of the DCM. The camera was mounted above the DCM so that the focal plane was parallel with the bending plane of the DCM. As shown in FIG. 17B, the DCM was assembled with two shape sensors embedded and then fixed at certain height. The DCM was controlled by pulling its drive cables with two linear sliding stages, each with an accuracy of 0.01 mm.

The drive cable was pulled, and stopped, in 0.8 mm increments to keep the DCM stable during data collection. The FBG sensing nodes' wavelengths and the camera image of DCM were recorded at each increment. The drive cables were pulled to the maximum 4 mm (bending cycle) and then released in 0.8 mm increments in order to return to the origin point (straightening cycle). Data at nine positions were recorded including five positions for the bending cycle and four positions for the straightening cycle. Each experiment was repeated five times.

Figures 18A, 18B, 18C:
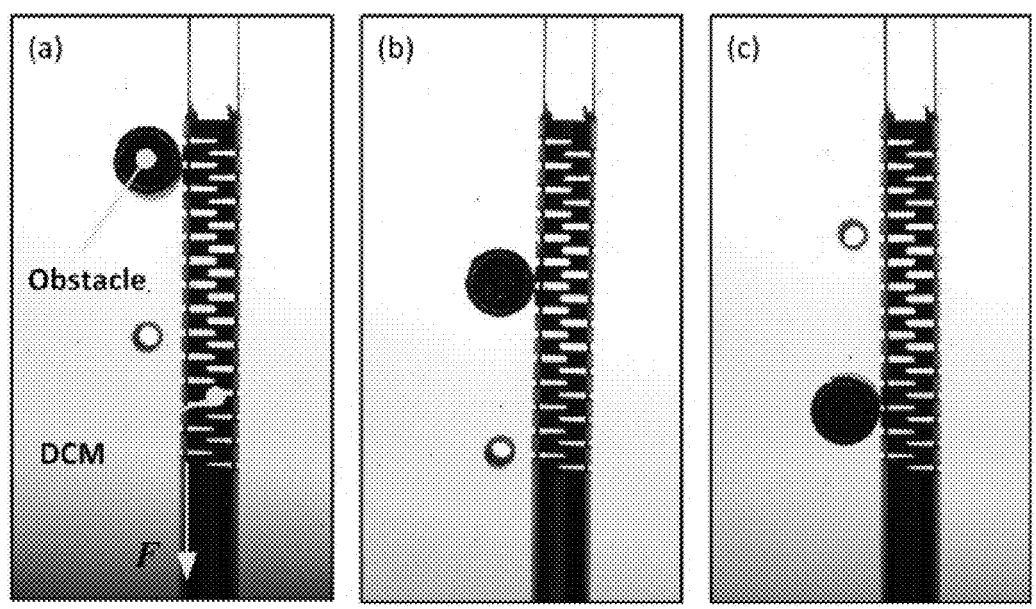
FIG. 18A shows a setup where the obstacle is near the distal tip (case I)
FIG. 18B shows a setup where the obstacle is in the middle of the bending segment (case II)
FIG. 18C shows a setup where the obstacle is near the proximal end (case III)

The path obstacles were placed in three positions on the same side when the DCM was straight, as shown in FIG. 18. In the figure, F represents the force applied to one of the drive cables. The obstacles were anticipated to create "S" shape deformation with at least one inflection point. Each obstacle configuration represents a scenario in which a portion of the DCM is obstructed from free bending within the lesion space. Obstacle cases II and III represent scenarios when a portion of the DCM is within the lesion space and the rest of the DCM is constrained by the screw hole of the acetabular implant (see FIG. 13 for detail).

DCM images taken by camera were processed with a 2D-3D registration method previously described in [5]. Using this method, the DCM outline in each camera image and the shape curve, defined by the DCM's centerline, are computed. Given the camera's intrinsic and extrinsic parameters, a 3D model of the DCM, and a kinematic/joint configuration of the DCM, the registration method simulates planar images of the DCM and then compares the simulated images with the true 2D camera images. This simulation process is run through an optimization algorithm over the possible DCM joint angles. The registration ensures a realistic, smooth, bend of the DCM by using a cubic spline with five control points to generate all 27 joint angles of the DCM. The joint angles determined by the registration process define the coordinate frames at each link of the DCM. The origins of each coordinate frame represent the DCM's centerline. The registration method approximates the DCM's tip position with an error less than 0.4 mm [6]. The difference between tip positions from the shape reconstruction and 2D-3D registration were used to evaluate the tracking accuracy of the shape sensors. For the accuracy evaluation we also compared the curvatures. The 29 points along the DCM's centerline, computed by the 2D-3D registration were fitted with a cubic spline and then curvature was analytically calculated.

Figure 19A:
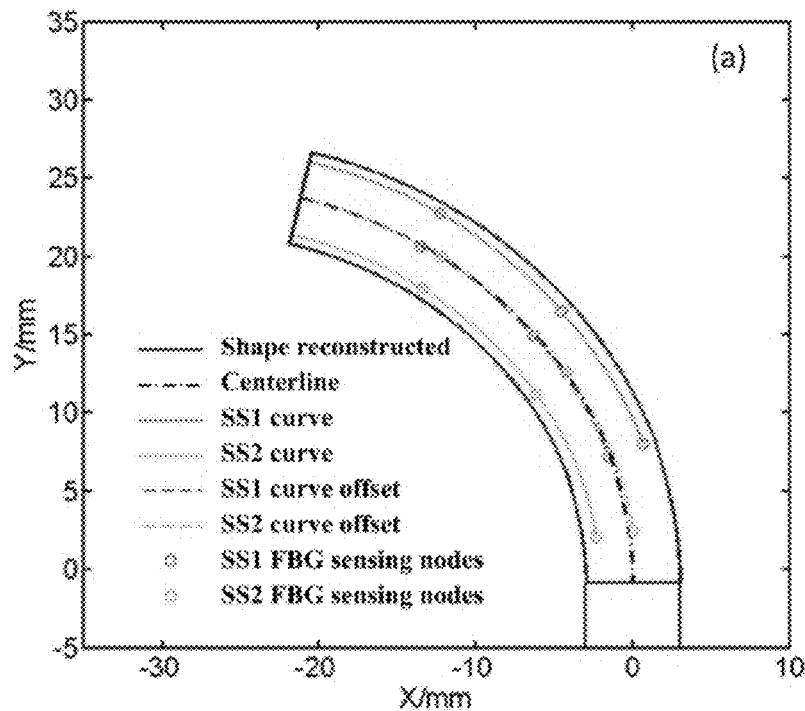
FIG. 19A shows a reconstructed DCM for a 4 mm pulling cable displacement.
Figure 19B:
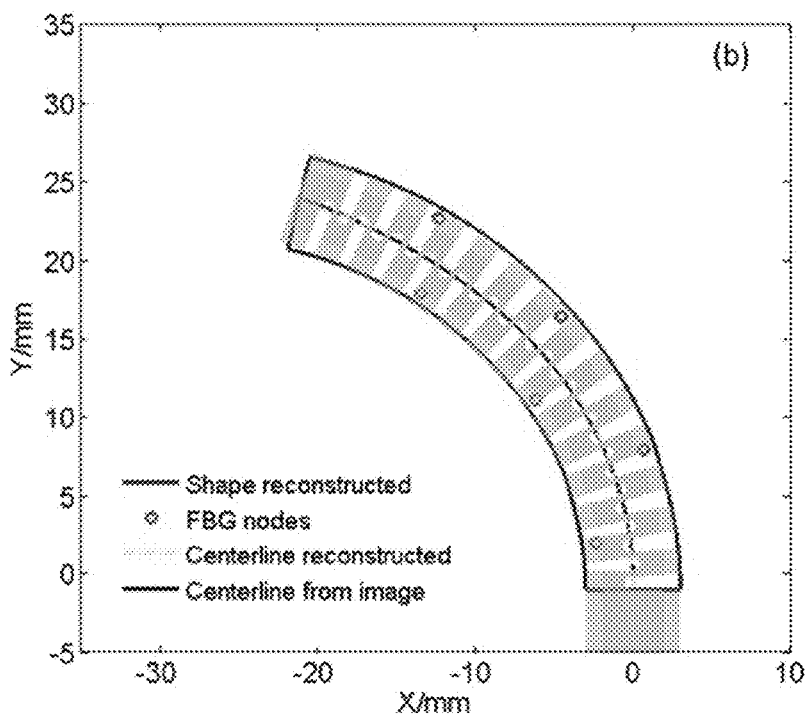
FIG. 19B shows the overlap of reconstructed and image extracted DCM under different driven cable displacements.

This experiment was repeated five times, each involving bending and release cycles with measurements at nine positions for each group. Forty-five shapes were reconstructed and images processed through 2D-3D registration. FIG. 19A displays one of the reconstructed shapes, showing the original sensor curves, their offset from the centerline, the final centerline, and the outline of the DCM. The FBG sensing nodes and their mapping points are also marked on the figure. In order to qualitatively verify consistent results, these images were superimposed on a model of the DCM generated from joint angles using 2D-3D registration method (FIG. 19B).

The average and standard deviation of the tip position error for each of the nine drive cable displacements are listed in Table 3. The overall distal tip tracking accuracy of the curvature sensor is 0.28±0.20 mm for bending, 0.48±0.34 mm for straightening and 0.41±0.30 mm for a bending/straightening cycle. To facilitate comparison with shape tracking research in the literature, tip error is normalized to the length of the DCM. The normalized accuracy is 1.1%+/−0.86%, and the maximum error is 3.4% for 35 mm length.

TABLE 3

The distal tip tracking accuracy for free bending

| Cable displacement/mm | Average error/ mm | Standard deviation of error/mm | Status |
|---|---|---|---|
| 0.8 | 0.18 | 0.072 | Bend |
| 1.6 | 0.12 | 0.017 | |
| 2.4 | 0.29 | 0.204 | |
| 3.2 | 0.35 | 0.217 | |
| 4.0 | 0.47 | 0.223 | |
| 3.2 | 0.97 | 0.220 | Straighten |
| 2.4 | 0.62 | 0.195 | |
| 1.6 | 0.40 | 0.147 | |
| 0.8 | 0.23 | 0.057 | |

Figure 20A:
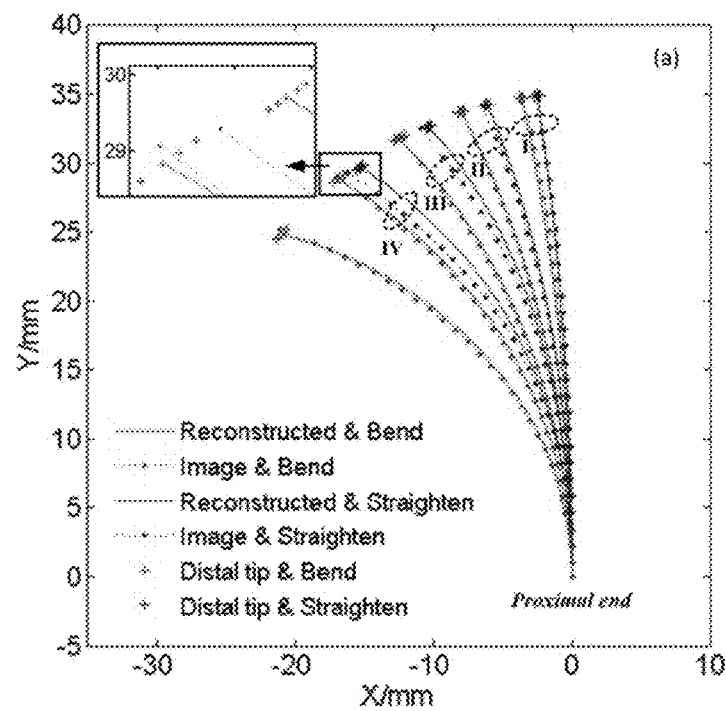
FIG. 20A shows the centerlines of both shape reconstruction and image extraction.
Figure 20B:
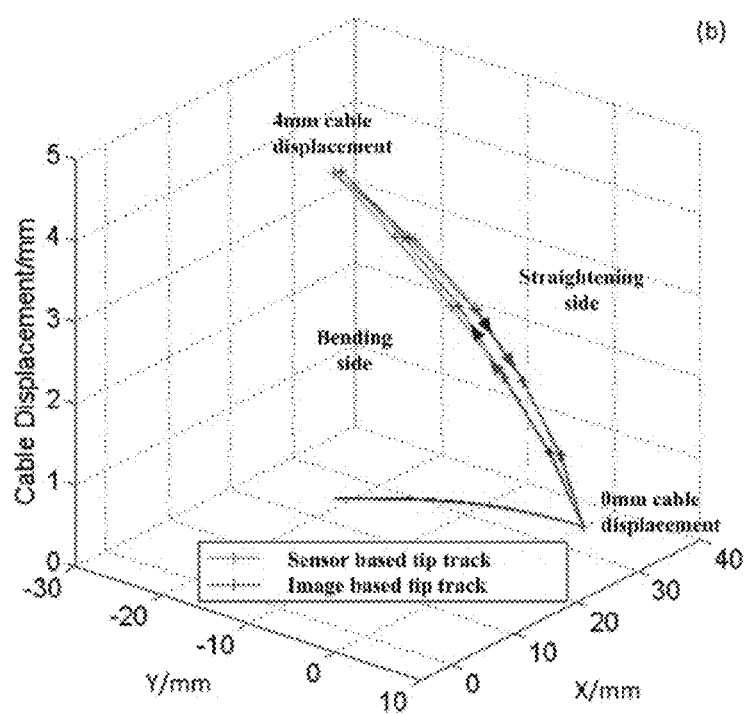
FIG. 20B shows the tip tracks of both shape reconstruction and image extraction.

FIG. 20A shows the comparison of DCM's centerlines between the ones reconstructed with FBG shape sensors and the ones extracted from images (on figures, 'reconstructed' is used to represent the calculated results with shape sensors, and 'image' is used to represent the extracted results from images captured by camera). Each shape curve represents the average of five experiments. Except for the largest bending, the other eight centerlines are in pairs (I, II, III and IV in FIG. 20A) involving identical drive cable displacements. Hysteric behavior of the DCM was observed by comparing the identical drive cable displacements during each pair's bending-straightening cycle. FIG. 20B displays the hysteresis of the tip position.

Figure 21:
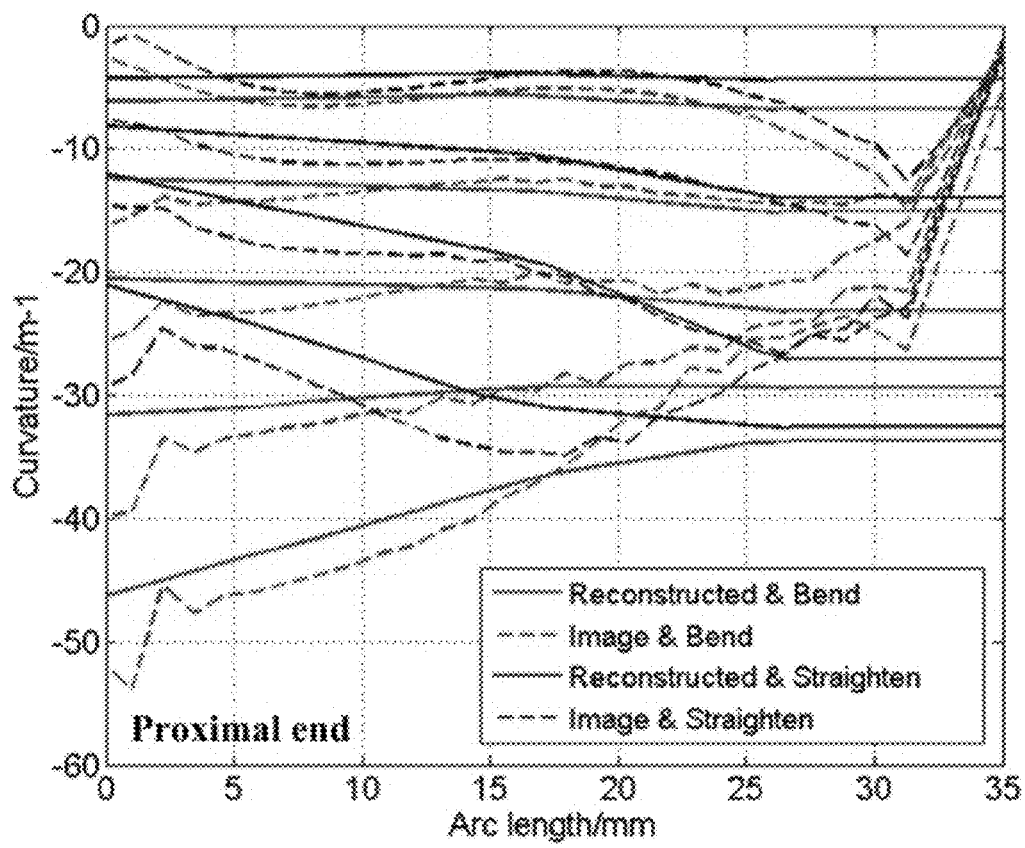
FIG. 21 shows a centerline curvature comparison for shape reconstruction and image extraction.

FIG. 21 illustrates the comparison of curvatures along the DCM's centerlines for both FBG calculated shape and 2D-3D registration methods. For the image extraction method, although the shape is smoothed before calculating the curvature, there is still fluctuation caused by limited joint position and spline interpolation method, especially for those points near proximal and distal end. For each drive cable length, the average curvature of the five groups is plotted. The figure also demonstrates hysteric behavior in bending/straightening cycles.

Figure 22A:
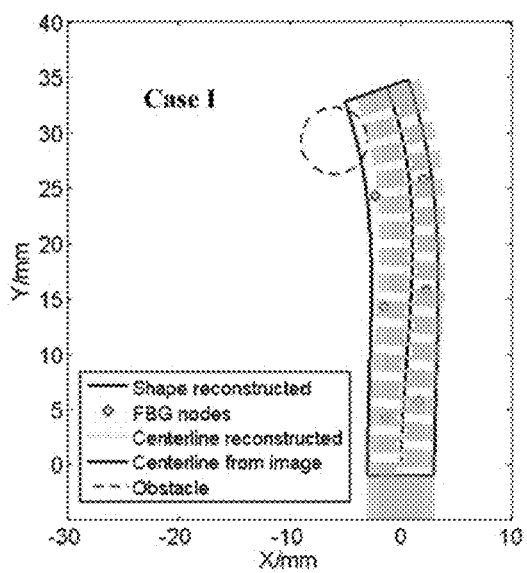
FIG. 22A illustrates an overlay of shape reconstructed for obstacle case I.
Figure 22B:
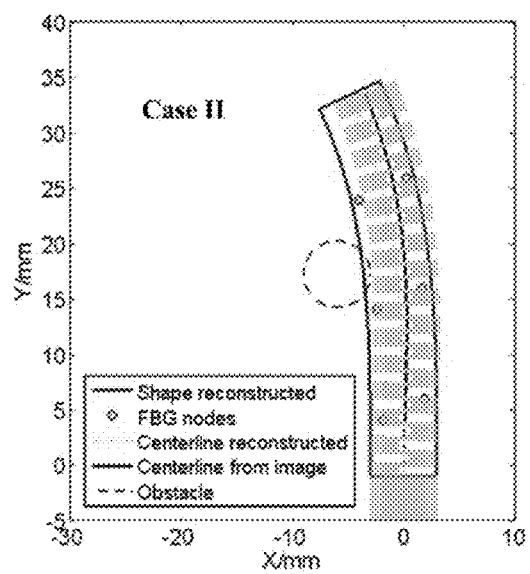
FIG. 22B illustrates an overlay of shape reconstructed for obstacle case II.
Figure 22C:
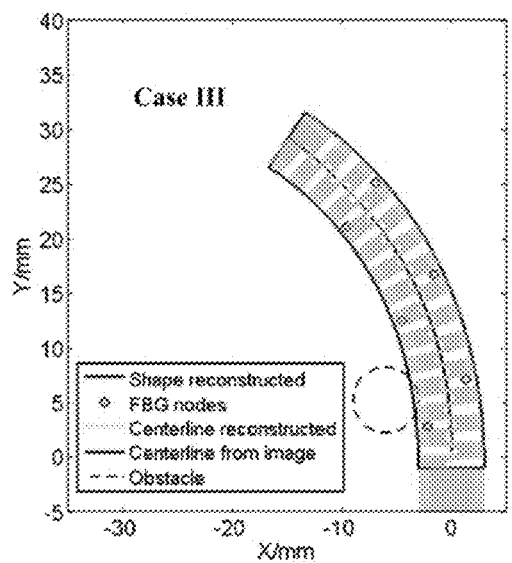
FIG. 22C illustrates an overlay of shape reconstructed for obstacle case III.
Figure 23A:
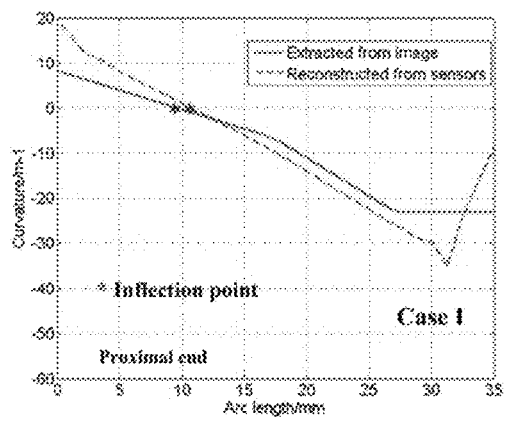
FIG. 23A provides a comparisons of the curvatures reconstructed from sensors and extracted from images for case I.
Figure 23B:
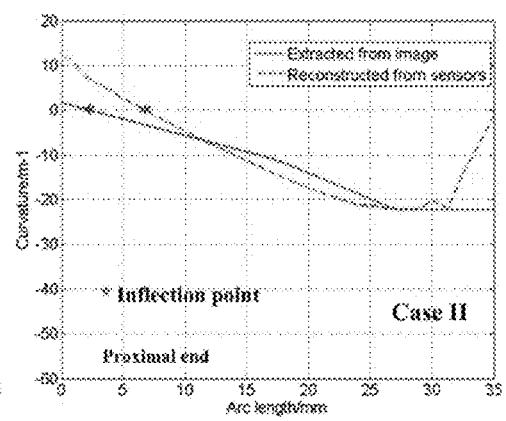
FIG. 23B provides a comparisons of the curvatures reconstructed from sensors and extracted from images for case II.
Figure 23C:
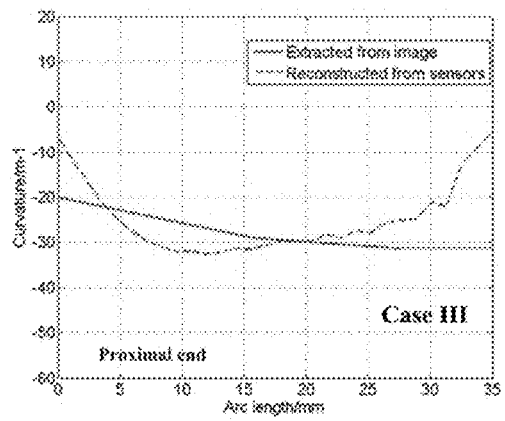
FIG. 23C provides a comparisons of the curvatures reconstructed from sensors and extracted from images for case III.

Table 4 lists the average and standard deviation of the distal tip tracking error for the bending with three different obstacle setups. FIGS. 22A-22C show the qualitative consistency of the results when superimposing the reconstructed shape from FBG sensors to that of the camera image obtained from 2D-3D registration. FIGS. 23A-23C show the curvatures obtained from camera images after 2D-3D registration change less drastically along the arc length.

TABLE 4

The distal tip tracking accuracy for bending with obstacle

| Cable displacement/ mm | Average error/ mm | Standard deviation of error/mm | Status |
|---|---|---|---|
| 0.8 | 0.75 | 0.040 | I |
| 1.6 | 0.47 | 0.052 | |
| 0.8 | 0.97 | 0.060 | II |
| 1.6 | 0.90 | 0.021 | |
| 0.8 | 0.33 | 0.06 | III |
| 1.6 | 0.24 | 0.08 | |
| 2.4 | 0.14 | 0.05 | |
| 3.2 | 0.21 | 0.11 | |

From FIGS. 19A and 19B and Table 3, it can be seen that the reconstructed shape with shape sensors matches well with the shape extracted via image processing. FIG. 21 illustrates that two shape sensors with three FBG sensing nodes on each have embodied the curvature tendency along the centerline. Thus, a limited number of FBG sensing nodes can achieve good tracking accuracy. From FIG. 19A, it can be seen that shape curves from the two shape sensors are not parallel; therefore, using the centerline of two shape sensors can get better accuracy than using the shape curve of a single shape sensor.

There are two major factors that cause error. The first source of error is the difference between the curvature used for shape reconstruction and the actual curvatures. The shape and curvature of the DCM vary along its length. The limited number of FBG sensing nodes and linear interpolation and extrapolation for curvature with arc length does not always work well. In FIG. 23C, the curvature shows non-linearity of approximately 10 mm from the proximal end, indicating that the curvature was not well captured at this point. The second source of error is the clearance between the shape sensor and its lumen on the DCM's wall. While the curvature readings were consistent and repeatable for the five sets of experiments, the clearance between the shape sensor and its lumen may cause curvature detection error.

Using more FBG sensing nodes may improve the accuracy for curvature estimation; however, as mentioned above, the number of FBG sensing nodes is restricted by the bandwidth of the interrogator and the wavelength range for each sensing node.

The most desirable placement for the shape sensors is along the neutral axis of the DCM. This will maintain the shape sensor length and position during bending. However, doing so may reduce the stiffness of the DCM, which would limit its effectiveness for the motivating orthopedic surgery.

Hysteresis was observed in all groups of free bending experiments (FIGS. 20A and 20B). The distal tip, shape curves, and curvature for each pair of positions all vary. The major difference in bending and straightening is observed at the proximal end of the DCM (FIG. 21). A major reason for this behavior, among others, may be the local friction force between the DCM slots and the drive cable during bending/straightening cycles.

From the tip tracking error listed in Table 4 and the shape overlay in FIG. 22A-22C, it can be seen that the tracking method remains effective even when there is an obstacle in the path of bending. For identical cable pulls, the tracking error in presence of obstacles is larger than free bending. This may be caused by the clearance between the shape sensor and its lumen. Even more so for the S shape observed in FIG. 22A-22C, the clearance will cause varying interaction between the shape sensor and its lumen, from the one obtained during calibration. FIG. 23A shows that the shape sensor can capture the S shape. From the image extracted curvature, there is an inflection point with zero curvature and the shape sensor successfully captures this inflection point. FIG. 23B also has an inflection point, but the shape sensor does not accurately capture this point. There is no inflection point on FIG. 23C. The presence of an inflection point is determined by the obstacle's position and stiffness of the DCM. The curvature tendency for case III is significantly different from the obstacle setups of I and II. For case III, the largest curvature occurs near the proximal end, and is not directly captured by the shape sensors. However, the overall accuracy for case III is better than cases I and II.

During the experiments, two shape sensors were observed to move along their lumens through the DCM wall. The distance the shape sensor travelled may be estimated to be the same as that of the drive cable because the drive cable and shape sensor lumens along the DCM wall are parallel. The average strain for six points are 0%, 2.29%, 4.57%, 6.86%, 9.14% and 11.43%. Herein, 1% from the FBG manufacture (Technica Optical Components, China) is set for the safe working strain of FBG optical fibers. The sensor will break under this strain, if the FBG optical fiber is fixed to the surface of the DCM. This proves that a novel large deflection shape sensing is necessary for this variation of DCM.

The difference between the inside and outside body temperatures during the surgery, in addition to operations such as tissue cutting or water injection, may create a temperature gradient along sensor nodes. The shape reconstruction method as described herein may compensate for such changes if the two adjacent FBG sensors are close enough with insignificant temperature gradient. The thermal conductivity of NiTi used as for the DCM body will help to minimize the temperature gradient along the sensor nodes.

The structure and thermal sensitivity of both shape sensors used were similar to those in [21, 22]. Moreover, there will be an opposite effect on wavelength shift at each of the sensors. This is because one sensor will be in compression (the inner side) and the opposing side's sensor (outer side) will be in tension. Therefore, the overall effect on the centerline may be reduced. Further study on the amount of temperature rise during the surgery may be required to justify these arguments.

We demonstrate the feasibility of large deflection shape tracking for a 35 mm length DCM using two shape sensors. The tracking scheme could well capture the DCM the shape for both free bending and bending with obstacles in the path. For the free bending case, the distal tip tracking accuracy was 0.28±0.20 mm for bending, 0.48±0.34 mm for straightening and 0.40±0.30 mm for bending/straightening cycle. The normalized accuracy was 1.1%+0.86%, and the maximum error was 3.4%. Hysteresis was observed during the bending/straightening cycle and accurately captured with the shape sensors. For the cases with obstacles, the tracking accuracy was 0.61±0.15 mm, 0.93±0.05 mm and 0.23±0.10 mm as obstacle was placed from distal to proximal location with respect to the DCM. The normalized accuracy was 1.7%±0.4%, 2.7%±0.2%, and 0.7%±0.3% respectively. The maximum error was 3.0%. This technique promises accurate tracking of the DCM for use in minimally invasive surgery; especially when working with large bending curvatures. Real-time shape tracking using FBG sensors combined with occasional accuracy verification (and possibly re-calibration) using x-ray images, may provide means for accurate, real-time, control of the DCM during minimally- and less-invasive procedures, and specifically for the treatment of osteolysis during total hip replacement.

References—Example 2

[1] R. J. Webster, J. M. Romano, and N. J. Cowan, (2009), Mechanics of precurved-tube continuum robots. Robotics, IEEE Transactions on, 25(1), 67-78.

[2] K. Ikuta, K. Yamamoto, and K. Sasaki, "Development of remote microsurgery robot and new surgical procedure for deep and narrow space," in Robotics and Automation, 2003. Proceedings. ICRA '03. IEEE International Conference on, 2003, pp. 1103-1108 vol. 1.

[3] M. D. M. Kutzer, S. M. Segreti, C. Y. Brown, M. Armand, R. H. Taylor, and S. C. Mears, Design of a new cable-driven manipulator with a large open lumen: Preliminary applications in the minimally-invasive removal of osteolysis. In Robotics and Automation (ICRA), 2011 IEEE International Conference on (pp. 2913-2920). IEEE

[4] R. J. Murphy, M. S. Moses, M. D. M. Kutzer, G. S. Chirikjian, and M. Armand, "Constrained workspace generation for snake-like manipulators with applications to minimally invasive surgery," in Robotics and Automation (ICRA), 2013 IEEE International Conference on, 2013, pp. 5341-5347.

[5] C. A. Engh, Jr., H. Egawa, S. E. Beykirch, R. H. Hopper Jr., and C. A. Engh, The quality of osteolysis grafting with cementless acetabular component retention, Clinical orthopaedics and related research, vol. 465, pp. 150-154, December 2007.

[6] Murphy, R. J., Kutzer, M. D., Segreti, S. M., Lucas, B. C., and Armand, M. (2013). Design and kinematic characterization of a surgical manipulator with a focus on treating osteolysis. Robotica, 1-16.

[7] Y. Otake, R. J. Murphy, M. D. Kutzer, R. H. Taylor, and A. Mehran, Piecewise-rigid 2D-3D registration for pose estimation of snake-like manipulator using an intraoperative x-ray projection. In SPIE Medical Imaging (pp. 90360Q-90360Q). International Society for Optics and Photonics, 2014

[8] M. Cianchetti, F. Renda, A. Licofonte, and C. Laschi, Sensorization of continuum soft robots for reconstructing their spatial configuration, Book Sensorization of continuum soft robots for reconstructing their spatial configuration (IEEE, 2012, edn.), pp. 634-639

[9] Shapiro, Y., Kósa, G., and Wolf, A.: Shape Tracking of Planar Hyper-Flexible Beams via Embedded PVDF Deflection Sensors, Mechatronics, IEEE/ASME Transactions on, 2014, 19, (4), pp. 1260-1267

[10] X. Yi, J. Qian, L. Shen, Y. Zhang and Z. Zhang, "An innovative 3D colonoscope shape sensing sensor based on FBG sensor array," in Information Acquisition, 2007. ICIA'07. International Conference on, pp. 227-232, 2007.

[11] Y. L. Park; S. Elayaperumal; B. Daniel; S. C. Ryu; M. Shin; J. Savall; R. J. Black; B. Moslehi; M. R. Cutkosky, "Real-Time Estimation of 3-D Needle Shape and Deflection for MRI-Guided Interventions," Mechatronics, IEEE/ASME Transactions on, vol. 15, no. 6, pp. 906, 915, December 2010

[12] R. J. Roesthuis, M. Kemp, van den Dobbelsteen, John J and S. Misra, "Three-dimensional needle shape reconstruction using an array of fiber bragg grating sensors," 2013.

[13] W. N. MacPherson, M. Silva-Lopez, J. S. Barton, A. Moore, J. Jones, D. Zhao, L. Zhang, I. Bennion, N. Metje and D. Chapman, "Tunnel monitoring using multicore fibre displacement sensor," Measurement Science and Technology, vol. 17, pp. 1180, 2006.

[14] X. F. Chen, C. Zhang, D. J. Webb, K. Kalli and P. Gang-Ding, "Highly sensitive bend sensor based on Bragg grating in eccentric core polymer fiber," IEEE Photonics Technology Letters, vol. 22, pp. 850-852, 2010.

[15] F. Araújo, L. Ferreira, J. Santos and F. Farahi, "Temperature and strain insensitive bending measurements with D-type fibre Bragg gratings," Measurement Science and Technology, vol. 12, pp. 829, 2001.

[16] J. P. Moore and M. D. Rogge, "Shape sensing using multi-core fiber optic cable and parametric curve solutions," Optics Express, vol. 20, pp. 2967-2973.

[17] H. Moon, J. Jeong, S. Kang, K. Kim, Yong-Won Song, Jinseok Kim, Fiber-Bragg-grating-based ultrathin shape sensors displaying single-channel sweeping for minimally invasive surgery, Optics and Lasers in Engineering, Volume 59, August 2014, Pages 50-55.

[18] H. Liu, A. Farvardin, S. A. Pedram, I. Iordachita, R. H. Taylor, M. Armand, Large Deflection Shape Sensing of a Continuum Manipulator for Minimally-Invasive Surgery, In Robotics and Automation (ICRA), 2015 IEEE International Conference on, Accepted.

[19] X. He, J. Handa, P. Gehlbach, R. H. Taylor and I. Iordachita, 'A submillimetric 3-dof force sensing instrument with integrated fiber bragg grating for retinal microsurgery', Biomedical Engineering, IEEE Transactions on, 2014, 61, (2), pp. 522-534

[20] R. M. Measures, Structural monitoring with fiber optic technology ISBN 0124874304: Academic, 2001.

[21] C. H. Lee, M. K. Kim, K. T. Kim and J. Lee, Enhanced temperature sensitivity of fiber Bragg grating temperature sensor using thermal expansion of copper tube. Microw. Opt. Technol. Lett., 2011, 53: 1669-1671.

[22] M. Esposito, S. Buontempo, A. Petriccione, M. Zarrelli, G. Breglio, A. Saccomanno, Z. Szillasi, A. Makovec, A. Cusano, A. Chiuchiolo, M. Bajko, M. Giordano, Fiber Bragg Grating sensors to measure the coefficient of thermal expansion of polymers at cryogenic temperatures, Sensors and Actuators A: Physical, 2013, 189: 195-203.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:
1. A shape sensor system, comprising:
a deflection sensor comprising an optical fiber having at least one fiber Bragg grating (FBG) written therein and a substrate, said optical fiber being attached to said substrate with a selected bias distance from a neutral plane of said deflection sensor;
an optical source optically coupled to said optical fiber to provide input light to be at least partially reflected by said FBG to provide output light; and
an optical detection and processing system arranged to receive at least a portion of said output light and to determine a wavelength shift of at least a portion of said output light resulting from a change of an amount of deflection of said deflection sensor, said optical detection and processing system being further configured to determine a relative amount of deflection of said deflection sensor at said FBG based on said wavelength shift,
wherein said selected bias distance is selected based on a predetermined range of deflection angles to be detected, and
wherein said substrate is a pair of wires attached to said optical fiber in a triangular configuration as viewed from a cross section thereof.
2. A shape sensor system according to claim 1, wherein said pair of wires are NiTi wires.
3. A shape sensor system according to claim 1, wherein a distance between said pair of wires in said triangular configuration is selected to obtain said selected bias distance.
4. A shape sensor system according to claim 1, wherein said optical fiber has a plurality of fiber Bragg gratings (FBGs) written therein,
wherein said optical source provides light with a plurality of distinguishable wavelength regions to simultaneously address said plurality of FBGs, and
wherein said optical detection and processing system is further configured to determine a plurality of wavelength shifts resulting from a plurality of changes of amounts of deflection of said deflection sensor, said optical detection and processing system being further configured to determine a plurality of relative amounts of deflection of said deflection sensor at said plurality of FBGs based on said plurality of wavelength shifts.
5. A flexible device, comprising:
a flexible elongated portion of said flexible device having a first end and a second end;
a shape sensor system comprising:
a deflection sensor comprising an optical fiber having at least one fiber Bragg grating (FBG) written therein and a substrate, said optical fiber being attached to said substrate with a selected bias distance from a neutral plane of said deflection sensor;

an optical source optically coupled to said optical fiber to provide input light to be at least partially reflected by said FBG to provide output light; and an optical detection and processing system arranged to receive at least a portion of said output light and to determine a wavelength shift of at least a portion of said output light resulting from a change of an amount of deflection of said deflection sensor, said optical detection and processing system being further configured to determine a relative amount of deflection of said deflection sensor at said FBG based on said wavelength shift, wherein said selected bias distance is selected based on a predetermined range of deflection angles to be detected, wherein said deflection sensor of said shape sensor system is slidably connected to said flexible elongated portion of said flexible device extending from said first end to said second end, and wherein said shape sensor system further comprises a plurality of deflection sensors slidably connected to said flexible elongated portion of said flexible device extending from said first end to said second end.

* * * * *

UNITED STATES PATENT AND TRADEMARK OFFICE
CERTIFICATE OF CORRECTION

PATENT NO. : 10,226,304 B2
APPLICATION NO. : 14/970177
DATED : March 12, 2019
INVENTOR(S) : Iulian Iordachita et al.

Page 1 of 1

It is certified that error appears in the above-identified patent and that said Letters Patent is hereby corrected as shown below:

In the Specification

Column 1, Line 9, please replace the second paragraph as follows:
STATEMENT OF GOVERNMENTAL INTEREST
This invention was made with government support under EB016703 awarded by the National Institutes of Health. The government has certain rights in the invention.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*